US005486473A

United States Patent [19]

Fujita et al.

[11] Patent Number: 5,486,473

[45] Date of Patent: Jan. 23, 1996

[54] A DNA CODING FOR A FLAVIVIRUS ANTIGEN

[75] Inventors: Hiroyuki Fujita, Mitoyo; Iwao Yoshida, Kanonzi; Mitsuo Takagi; Sadao Manabe, both of Mitoyo; Konosuke Fukai, Toyonaka, all of Japan

[73] Assignee: The Research Foundation for Microbial Diseases of Osaka University, Osaka, Japan

[21] Appl. No.: 194,049

[22] Filed: Feb. 9, 1994

Related U.S. Application Data

[63] Continuation of Ser. No. 809,255, Dec. 18, 1991, abandoned, which is a continuation of Ser. No. 279,685, Dec. 5, 1988, abandoned, which is a continuation-in-part of Ser. No. 932,419, Nov. 19, 1986, Pat. No. 4,810,492.

[30] Foreign Application Priority Data

May 6, 1986 [JP] Japan .................................. 61-131208

[51] Int. Cl.$^6$ .............................. C12N 5/10; C12N 1/21; C12N 15/40; C12N 15/70

[52] U.S. Cl. ................................. 435/240.2; 435/252.33; 435/320.1; 536/23.72

[58] Field of Search ........................ 536/23.72; 435/69.3, 435/252.3, 320.1; 424/89; 530/350; 935/81

[56] References Cited

U.S. PATENT DOCUMENTS 4,358,535 11/1982 Falkow et al. ............................ 435/34
4,902,783 2/1990 Goda et al. ............................ 435/69.1
5,010,000 4/1991 Palva ......................................... 435/231
5,021,347 6/1991 Yasui ...................................... 435/235.1

OTHER PUBLICATIONS

Ellis et al., (1985), Journal of Virology, vol. 53, No. 1, pp. 81–88 (Abstract).
Takegami et al., (1982), Acta Virol., vol. 26, pp. 321–327.
Huynh et al., (1985), "Constructing and Screening cDNA Libraries in λgt10 and λgt11", in *DNA Cloning* ed, Glover (IRL Press, Oxford, UK).
Sumiyoshi et al., (1986), "Sequence of 3000 Nucleotides at the 5' End of Japanese Encephalitis Virus RNA", Gene, vol. 48, pp. 195–201.
Igarashi, *J. Gen. Virol.*, 40, 531 (1978).
Kimura–Kuroda et al., *J. Virol.*, 45, 124 (1983).
Kobayashi et al., *Infect. Immun.*, 44, 117 (1984).
Wengler et al., *Virol.*, 147, 264 (1985).
Rice et al., *Science*, 229, 726 (1985).
Kogaku, *Cell Technol.*, 3, 97 (1984) in Japanese.

*Primary Examiner*—Mindy Fleisher
*Assistant Examiner*—James Ketter
*Attorney, Agent, or Firm*—Armstrong, Westerman, Hattori, McLeland & Naughton

[57] ABSTRACT

There is disclosed a DNA which codes for an antigen comprising at least part of an amino acid sequence of the antigen of a flavivirus, which part contains at least one epitope of the flavivirus antigen. The present DNA can be used for producing the antigen easily and safely at low cost by means of recombinant DNA technique. The antigen produced using the present DNA can be used as an effective vaccine and diagnostic for Japanese encephalitis.

5 Claims, 20 Drawing Sheets

```
                 10                  20                      30                  40                  50                  60
TTT AAT TGT CTG GGA ATG GGC AAT CGT GAC TTC ATA GAA GGA GCC AGT GGA GCC ACT TGG
Phe Asn Cys Leu Gly Met Gly Asn Arg Asp Phe Ile Glu Gly Ala Ser Gly Ala Thr Trp
TTC AAC TGT TTA GGA ATG AGT AAC AGA GAC TTC CTG GAG GGA GTG TCT GGA GCT ACA TGG
*** *** *** *** *** *** Ser *** *** *** *** Leu *** *** Val *** *** *** *** ***
GCT CAC TGC ATT GGA ATT ACT GAC AGG GAT TTC ATT GAG GGG GTG CAT GGA GGA ACT TGG
Ala His *** Ile *** Ile Thr Asp *** *** *** *** *** *** Val His *** Gly *** ***

                 70                  80                  90                 100                 110                 120
GTG GAC TTG GTG CTA GAA GGA GAT AGC TGC TTG ACA ATC ATG GCA AAC GAC AAA CCA ACA
Val Asp Leu Val Leu Glu Gly Asp Ser Cys Leu Thr Ile Met Ala Asn Asp Lys Pro Thr
GTT GAT CTG GTA CTG GAA GGC GAT AGT TGT GTG ACC ATA ATG TCA AAA GAC AAG CCA ACC
*** *** *** *** *** *** *** *** *** *** Val *** *** *** Ser Lys *** *** *** ***
GTT TCA GCT ACC CTG GAG CAA GAC AAG TGT GTC ACT GTT ATG GCC CCT GAC AAG CCT TCA
*** Ser Ala Thr *** *** Gln *** Lys *** Val *** Val *** *** Pro *** *** *** Ser
```

FIG. 1a

```
                    130                 140                 150                 160                 170                 180
TTG GAC GTC CGC ATG ATT AAC ATC GAA GCT CAA AGC CAA CTT GCT GAG GTC AGA AGT TAC TGC
Leu Asp Val Arg Met Ile Asn Ile Glu Ala Gln Ser Gln Leu Ala Glu Val Arg Ser Tyr Cys
ATT GAT GTC AAA ATG ATG AAC ATG GAA GCA GCC CTC GCA GAT CGC GTG CGC AGT TAC TGT
Ile Asp Val Lys Met Met Asn Met Glu Ala Ala Leu Ala Asp Arg Val Arg Ser Tyr Cys
*** **** **** **** **** *** *** **** **** **** **** **** **** **** **** **** **** ****
TTG GAC ATC TCA CTA GAG ACA GTA GCC ATT GAT AGA CCT GCT GAG GTG AGG AAA GTG TGT
Leu Asp Ile Ser Leu Glu Thr Val Ala Ile Asp Arg Pro Ala Glu Val Arg Lys Val Cys
*** *** *** *** *** *** *** *** *** *** *** *** *** *** *** *** *** *** *** ***

                    190                 200                 210                 220                 230                 240
TAT CAT GCT TCA GTC ACT GAC ATC TCG ACG GTG GCT CCC ACG GGA GAT CGT GGA GCT
Tyr His Ala Ser Val Thr Asp Ile Ser Thr Val Ala Pro Thr Gly Asp Arg Gly Ala
TAC CTA GCT TCG GTC AGT GAC TTG TCA ACA AGA GCG TGT CCA ACC ATG GGT GAA GCC
Tyr Leu Ala Ser Val Ser Asp Leu Ser Thr Arg Cys Pro Thr Met Gly Glu Ala
*** **** **** **** **** *** *** **** **** **** **** **** **** **** **** ****
TAC AAT GCA GTT CTC ACT CAT GTG AAG ATT AAT GAC TGC AGC GTG ACT GGA GAG GGC
Tyr Asn Ala Val Leu Thr His Val Lys Ile Asn Asp Cys Ser Val Thr Gly Glu Gly
*** *** *** *** *** *** *** *** *** *** *** *** *** *** *** *** *** *** ***

                    250                 260                 270                 280                 290                 300
CAC AAC GAG AAG CGA GCT GAT AGT AGC TAT GTG TGC AAA CAA GGC TTC ACT GAT CGT GGG
His Asn Glu Lys Arg Ala Asp Ser Ser Tyr Val Cys Lys Gln Gly Phe Thr Asp Arg Gly
CAC AAC GAG AAA AGA GCT GCT GAC CCC GCC TTC GTT TGC AAG CAA GGC GTT GTG GAC AGA GGA
His Asn Glu Lys Arg Ala Ala Asp Pro Ala Phe Val Cys Lys Gln Gly Val Val Asp Arg Gly
*** **** **** **** **** **** **** **** **** **** **** **** **** **** **** **** ****
CAC CTA GCT GAA GAG AAC GAC GGG GAA AAC GCG TGC AAG TGC TAT TCT GAT AGA GGC
His Leu Ala Glu Glu Asn Asp Gly Glu Asn Ala Cys Lys Cys Tyr Ser Asp Arg Gly
*** *** *** *** *** *** *** *** *** *** *** *** *** *** *** *** *** *** ***
```

FIG. 1b

```
                310         320         330         340         350         360
TGG GGC AAC GGA TGT GGA CTT TTC GGG AAG GGA AGC ATT GAC ACA TGT GCA AAA TTC TCC
Trp Gly Asn Gly Cys Gly Leu Phe Gly Lys Gly Ser Ile Asp Thr Cys Ala Lys Phe Ser
*** **** *** **** *** *** *** *** *** *** *** *** *** **** *** *** *** *** *** ***
TGG GGA AAT GGC TGC GGA CTG TTT GGA AAG GGA AGC ATT GAC ACA TGT GCG AAG TTT GCC
Trp Gly Asn Gly Cys Gly Leu Phe Gly Lys Gly Ser Ile Asp Thr Cys Ala Lys Phe Ala
*** **** *** **** *** *** *** *** *** *** *** *** *** **** *** *** *** *** *** ***
TGG GGC AAT GGC TGT GGC CTA TTT GGC TTT GGG AGC ATT GAC ACA TGC GCC AAA TTC ACT
Trp Gly Asn Gly Cys Gly Leu Phe Gly Phe Gly Ser Ile Asp Thr Cys Ala Lys Phe Thr
*** **** *** **** *** *** *** *** *** *** *** *** *** **** *** *** *** *** *** ***
                                                *** **** *** **** *** **** *** *** *** ***
*** *** *** *** *** *** *** *** *** *** *** *** Val Ala *** **** *** **** *** Val

                370         380         390         400         410         420-
TGC ACC AGC AAA GCG ATT GGA AGA ACA ATC CAG CCA GAA AAC ATC AAA TAC GAA GTT GGC
Cys Thr Ser Lys Ala Ile Gly Arg Thr Ile Gln Pro Glu Asn Ile Lys Tyr Glu Val Gly
TGT ACA ACC AAA GCA ACT GGA TGG ATC ATC CAG AAG GAA AAC ATC AAG TAT GAG GTT GGT
Cys Thr Thr Lys Ala Thr Gly Trp Ile Ile Gln Lys Glu Asn Ile Lys Tyr Glu Val Gly
**** *** **** *** *** *** *** Trp TTG *** **** *** **** *** **** *** *** *** ***
Thr *** **** *** *** *** *** Trp Leu *** **** *** **** *** **** *** *** *** Ala
TGT GCC --- AAA TCC AGT ATG TTT --- TTT GAG GTT GAT CAG ACC AAA ATT CAG TAT GTC
Cys Ala     Lys Ser Ser Met Phe     Phe Glu Val Asp Gln Thr Lys Ile Gln Tyr Val
*** *** --- *** *** *** *** Leu --- *** *** *** *** *** *** *** *** *** *** ***
*** Ala     Ser Met Ser Leu         Phe Glu Val Asp Gln Thr *** Ile Gln Tyr Val

                430         440         450         460         470         480
ATT TTT GTG CAT GGA ACC ACT TCG GAA AAC CAT GGG AAT TAT TCA GCG CAA GTT GGG
Ile Phe Val His Gly Thr Thr Ser Glu Asn His Gly Asn Tyr Ser Ala Gln Val Gly
ATA TTT GTG CAT GGC CCG ACG GAA GTT CAT GGC AAG --- --- --- GCG GCA GGG
Ile Phe Val His Gly Pro Thr Glu Val His Gly Lys         --- Ala Ala Gly
*** *** *** *** *** *** *** *** Val *** *** *** *** *** *** *** *** *** ATA ***
*** Phe *** *** *** *** *** Val Ser *** Lys --- --- --- --- Asp Ile Ile
ATC AGA GCA CAA TTG CAT GTA GGG GCC CAG GAA AAT TGG AAT ACC GAC ATT ---
Ile Arg Ala Gln Leu His Val Gly Ala Gln Glu Asn Trp Asn Thr Asp Ile
*** *** *** *** *** *** *** *** *** *** Glu --- --- *** *** *** *** Ile
*** Arg Ala Gln Leu His Val Gly Ala Gln Glu     --- Trp Asn Thr Asp Ile
```

FIG. 1c

```
                    490              500              510              520              530              540
GCG TCC CAG GCG GCA AAG TTT ACA ATA ACA CCC AAT GCT CCT TCG ATA ACC CTC GGG CTT
Ala Ser Gln Ala Ala Lys Phe Thr Ile Thr Pro Asn Ala Pro Ser Ile Thr Leu Gly Leu
*** --- --- --- *** --- *** --- *** *** *** --- *** *** *** *** *** *** *** ***
GCC ACC CAG GCT GGA AGA TTC AGT ATA ACT CCA GCG TCT TAC ACG TAC AAG CTA TTG
Ala Thr Gln Ala Gly Arg Phe Ser Ile Thr Pro Ala Ser Tyr Thr Tyr Lys Leu Ile
*** --- --- *** --- *** AAG *** --- *** *** *** **** **** **** **** **** **** **** ****
--- --- --- *** AAG ACT CTC AAG TTT --- GAT GCC CTG TCA GGC TCC CAG GAA GTC TTC ATT
--- --- --- *** Lys Thr Leu Lys Phe --- Asp Ala Leu Ser Gly Ser Gln Glu Val Phe Ile
--- --- --- --- Lys Thr Leu *** *** --- Asp Ala Leu Ser Gly Ser Gln Val Glu Phe Ile

                    550              560              570              580              590              600
GGT GAC TAC GGA GAA GTC ACG CTG GAC TGT GAG CCA AGG AGT GGA CTG AAC ACT GAA GCG
Gly Asp Tyr Gly Glu Val Thr Leu Asp Cys Glu Pro Arg Ser Gly Leu Asn Thr Glu Ala
GGT GAG TAT GGT GAG TTT ACG GAT GTT TGT GAG CCA TCA CGG ATA GAC AGC GCC
Gly Glu Tyr Gly Glu Phe Thr Asp Val Cys Glu Pro Ser Arg Ile Asp Ser Ala
*** **** **** **** **** *** **** *** **** *** **** **** **** **** **** **** **** **** **** ***
GGG --- TAT GGA AAA GCT ACA *** TGC CAG GTG CAA ACT GCG GTG GAC TTT GGT AAC
Gly --- Tyr Gly Lys Ala Thr *** Cys Gln Val Gln Thr Ala Val Asp Phe Gly Asn
*** --- *** *** Lys Ala *** *** Glu *** Gln Val *** Gln Thr Ala Val Asp *** Gly Asn

                    610              620              630              640              650              660
TTT TAC GTC ATG ACC GTG GGG TCA AAG TCA TTT CTG GTC CAT AGG GAA TGG TTT CAT GAC
Phe Tyr Val Met Thr Val Gly Ser Lys Ser Phe Leu Val His Arg Glu Trp Phe His Asp
TAT TAC GTT ATG TCA GGT GTT AAG TCC TTC CTG GTT CAC CGA GAA TGG TTT ATG GAT
Tyr Tyr Val Met Ser Gly Val Lys Ser Phe Leu Val His Arg Glu Trp Phe Met Asp
*** *** *** *** **** **** **** *** *** **** **** **** **** **** **** **** *** **** **** ***
AGT TAC ATC GCT GAG ATG GAG ACA *** ATA GTG GAC AGA *** TGG GCC CAG GAC
Ser Tyr Ile Ala Glu Met Glu Thr *** Ile Val Asp Arg *** Trp Ala Gln Asp
Ser *** *** Ile Ala Glu Glu Thr Glu *** Trp Ile *** Asp Asp *** *** Ala Gln ***
```

FIG. 1d

```
                670                 680                 690                 700                 710                 720
CTC GCT CTC CCC TGG ACG TCC CCT TCG AGC ACA GCG TGC AGA AAC AGA GAA CTC CTC ATG
Leu Ala Leu Pro Trp Thr Ser Pro Ser Ser Thr Ala Cys Arg Asn Arg Glu Leu Leu Met
CTG AAC CTG CCA TGG AGC AGT GCT GGA AGC ACC ACG TGG AGG AAC CGG GAA ACA CTG ATG
*** Asn *** *** *** Ser *** Ala Gly *** *** Thr Trp *** *** *** *** Thr *** ***
TTG ACC CTG CCA TGG CAG AGT GGA AGT GGC GGG GTG TGG AGA GAG ATG CAT CAT CTT GTC
*** Thr *** *** *** Gln *** Gly *** Gly Gly Val Trp *** Glu Met His His *** Val

            730                 740                 750                 760                 770                 780
GAA TTT GAA GAG GCG CAC GCC ACA AAA CAG TCC GTT GTT GCT CTT GGG TCA CAG GAA GGA
Glu Phe Glu Glu Ala His Ala Thr Lys Gln Ser Val Val Ala Leu Gly Ser Gln Glu Gly
GAG TTT GAA GAA CCT CAT GCC ACC AAA CAA TCT GTT GTG GCT CTA GGG TCG CAG GAA GGT
*** *** *** *** Pro *** *** *** *** *** *** *** *** *** *** *** *** *** *** ***
GAA TTT GAA CCT CCG CAT GCC GCC ACT ATC AGA GTA CTG GCC CTG GGA AAC CAG GAA GGC
*** *** *** Pro Pro *** *** Ala Thr Ile Arg *** Leu *** *** *** Asn *** *** ***

            790                 800                 810                 820                 830                 840
GGC CTC CAT CAG GCG TTG GCA GGA GCC ATC GTG GTG --- --- --- --- GAG TAC TCA AGC
Gly Leu His Gln Ala Leu Ala Gly Ala Ile Val Val --- --- --- --- Glu Tyr Ser Ser
GCG TTG CAC CAA GCT CTG GCC GGA GCG ATT CCT GTT --- --- --- --- GAG TTC TCA AGC
Ala *** *** *** *** *** *** *** *** *** Pro *** --- --- --- --- *** Phe *** ***
TCC TTG AAA ACA GCT CTT ACT GGC GCA ATG AGG GTT ACA AAG GAC ACA AAT GAC AAC AAC
Ser *** Lys Thr *** *** Thr *** *** Met Arg *** Thr Lys Asp Thr Asn Asp Asn Asn
```

FIG. 1e

```
                850                 860                 870                     880                 890                 900
--- TCA GTG AAG TTA ACA TCA GGC CAC CTG AAA TGT AGG ATG AAA ATG GAC AAA CTG GCT
--- Ser Val Lys Leu Thr Ser Gly His Leu Lys Cys Arg Met Lys Met Asp Lys Leu Ala
AAC ACT GTG AAG TTG ACA TCA GGA CAT CTG AAG TGT CGG GTG AAG ATG GAG AAG TTG CAG
Asn Thr *** *** *** *** *** *** *** *** *** *** *** Val *** *** Glu *** *** Gln
--- CTT TAC AAA CTA CAT GGT GGA CAT GTT TCT TGC AGA GTG AAA TTG TCA GCT TTG ACA
--- Leu Tyr *** *** His Gly *** *** Val Ser *** *** Val *** Leu Ser Ala *** Thr

                910                 920                 930                     940                 950                 960
CTG AAA GGC ACA ACC TAT GGC ATG TGT ACA GAA AAA TTC TCG TTC GCG AAA AAT CCG GCG
Leu Lys Gly Thr Thr Tyr Gly Met Cys Thr Glu Lys Phe Ser Phe Ala Lys Asn Pro Ala
CTG AAG GGA ACA ACA TAT GGA GTA TGT TCA AAA GCG TTC AAA TTC GCT AGG ACT CCC GCT
*** *** *** *** *** *** *** Val *** Ser Lys Ala *** Lys *** *** Arg Thr *** ***
CTC AAG GGG ACA TCC TAC AAA ATA TGC ACT GAC AAA ATG TTT TTT GTC AAG AAC CCA ACT
*** *** *** *** Ser *** Lys Ile *** *** Asp *** Met Phe *** Val *** *** *** Thr

                970                 980                 990                    1000                1010                1020
GAC ACT GGC CAC GGA ACA GTT GTC ATT GAA CTA TCC TAC TCT GGG AGT GAT GGC CCC TGC
Asp Thr Gly His Gly Thr Val Val Ile Glu Leu Ser Tyr Ser Gly Ser Asp Gly Pro Cys
GAC ACT GGC CAC GGA ACG GTG GTG TTG GAA CTG CAA TAT ACC GGA ACA GAC GGT CCC TGC
*** *** *** *** *** *** *** *** Leu *** *** Gln *** Thr *** Thr *** *** *** ***
GAC ACT GGC CAT GGC ACT GTT GTG ATG CAG GTG AAA GTG TCA AAA GGA --- GCC CCC TGC
*** *** *** *** *** *** *** *** Met Gln Val Lys Val *** Lys Gly --- Ala *** ***
```

FIG. 1f

```
                1030            1040            1050             1060            1070            1080
AAA ATT CCG ATT GTC TCC GTT GCG AGC CTC AAT GAC ATG ACC CCC GTT GGG CGG CTG GTG
Lys Ile Pro Ile Val Ser Val Ala Ser Leu Asn Asp Met Thr Pro Val Gly Arg Leu Val
AAA GTG CCC ATT TCT TCC GTA GCT TCC CTG AAT GAC CTC ACA CCT GTT GGA AGA CTG GTG
*** Val *** *** Ser *** *** *** *** *** *** *** Leu *** *** *** *** *** *** ***
AGG ATT CCA GTG ATA GTA GCT GAT GAT CTT ACA GCG GCA ATC AAT AAA GGC ATT TTG GTT
Arg *** *** Val Ile Val Ala Asp Asp *** Thr Ala Ala Ile Asn Lys *** Ile *** ***

                1090            1100            1110             1120            1130            1140
ACA GTG AAC CCT TTC GTC GCG ACT TCC AGT GCC AAC TCA AAG CTG CTG GTC GAG ATG GAA
Thr Val Asn Pro Phe Val Ala Thr Ser Ser Ala Asn Ser Lys Leu Leu Val Glu Met Glu
ACC GTG AAT CCA TTT GTG TCT GTG GCC ACA GCC AAC TCG AAG GTT TTG ATT GAA CTC GAA
*** *** *** *** *** *** Ser Val Ala Thr *** *** *** *** Val *** Ile *** Leu ***
ACA GTT AAC CCC ATC GCC TCA ACC --- --- AAT GAT GAT GAA GTG CTG ATT GAG GTG AAC
*** *** *** *** Ile Ala Ser *** --- --- Asn Asp Asp Glu Val *** Ile *** Val Asn

                1150            1160            1170             1180            1190            1200
CCC CCC TTC GGA GAC TCC TAC ATC GTG GTT GGG AGG GGA GAC AAG CAG ATC AAC CAC CAT
Pro Pro Phe Gly Asp Ser Tyr Ile Val Val Gly Arg Gly Asp Lys Gln Ile Asn His His
CCC CCG TTT GGT GAC TCT TAC ATC GTG GTG GGA AGA GGA GAA CAG CAG ATA AAC CAT CAC
*** *** *** *** *** *** *** *** *** *** *** *** *** Glu Gln *** *** *** *** ***
CCA CCT TTT GGA GAC AGC TAC ATT ATC GTT GGG AGA GGA GAT TCA CGT CTC ACT TAC CAG
*** *** *** *** *** *** *** *** Ile *** *** *** *** *** Ser Arg Leu Thr Tyr Gln
```

FIG. 1g

```
                1210                1220                1230                1240                1250                1260
TGG CAC AAA GCT GGA AGC ACG CTA GGC AAG GCC TTT TCA ACA ACT TTG AAG GGA GCT CAA
Trp His Lys Ala Gly Ser Thr Leu Gly Lys Ala Phe Ser Thr Thr Leu Lys Gly Ala Gln
TGG CAC AAA TCT GGG AGC AGC ATT GGA AAG GCC TTT ACC ACC ACA CTC AGA GGA GCT CAA
*** *** *** Ser *** *** Ser Ile *** *** *** *** Thr *** *** *** Arg *** *** ***
TGG CAC AAA GAG GGA AGC TCA ATA GGA AAG TTG TTC ACT CAG ACC ATG AAA GGC GTG GAA
*** *** *** Glu *** *** Ser Ile *** *** Leu *** Thr Gln *** Met *** *** Val Glu

                1270                1280                1290                1300                1310                1320
AGA CTG GCA GCG TTG GGC GAC ACA GCC TGG GAC TTT GGC TCC ATT GGA GGG GTC TTC AAC
Arg Leu Ala Ala Leu Gly Asp Thr Ala Trp Asp Phe Gly Ser Ile Gly Gly Val Phe Asn
CGA CTC GCA GCT CTT GGA GAT ACT GCT TGG GAT TTT GGA TCA GTT GGA GGG GTT TTC ACC
*** *** *** *** *** *** *** *** *** *** *** *** *** *** Val *** *** *** *** Thr
CGC CTG GCC GTC ATG GGA GAC ACC GCC TGG GAT TTC AGC TCC GCT GGA GGG TTC TTC ACT
*** *** *** Val Met *** *** *** *** *** *** *** Ser *** Ala *** *** Phe *** Thr

                1330                1340                1350                1360                1370                1380
TCC ATA GGA AAA GCC GTT CAC CAA GTG TTT GGT GGT GCC TTC AGA ACA CTC TTT GGG GGA
Ser Ile Gly Lys Ala Val His Gln Val Phe Gly Gly Ala Phe Arg Thr Leu Phe Gly Gly
TCA GTG GGG AAA GCC ATA CAC CAA GTC TTT GGA GGA GCT TTT AGA TCA CTC TTT GGA GGG
*** Val *** *** *** Ile *** *** *** *** *** *** *** *** *** Ser *** *** *** ***
TCG GTT GGG AAA GGA ATT CAT ACG GTG TTT GGC TCT GCC TTT CAG GGG CTA TTT GGC GGC
*** Val *** *** Gly Ile *** Thr *** *** *** Ser *** *** Gln Gly *** *** *** ***
```

FIG. 1h

```
         1390            1400            1410            1420            1430            1440
ATG      TCT  ACA  ATC  TGG  CAA  GGG  CTA  ATG  GCC  CTA  CTC  TGG  ATG  GGC  GTC  AAC  GCA
Met      Ser  Thr  Ile  Trp  Gln  Gly  Leu  Met  Ala  Leu  Leu  Trp  Met  Gly  Val  Asn  Ala
ATG      TCC  ACA  ATC  TGG  ACA  GGA  CTT  CTG  GCT  CTT  CTG  TTG  ATG  GGA  ATC  AAT  GCC
Met      Ser  Thr  Ile  Trp  Thr  Gly  Leu  Leu  Ala  Leu  Leu  Leu  Met  Gly  Ile  Asn  Ala
***      **** **** **** **** **** **** **** **** **** **** **** **** **** **** **** **** ****
TTG      AAC  ACA  ATA  AAG  ATG  GTC  ATC  ATG  GCG  GTA  CTT  ATA  TGG  GGC  ATC  AAC  ACA
Leu      Asn  Thr  Ile  Lys  Met  Val  Ile  Met  Ala  Val  Leu  Ile  Trp  Gly  Ile  Asn  Thr
***      **** **** **** **** **** **** **** **** **** **** **** **** **** **** **** **** ****
Leu      Asn       Ile       Lys       Val  Ile       Val       Val  Ile  Val       Ile       Thr

         1450            1460            1470            1480            1490            1500
CGA      GAC  TCA  ATT  GCT  TTG  GCC  TTC  GCC  ACA  GGA  GGT  GTG  CTC  GTG  TTC  TTA  GCG
Arg      Asp  Ser  Ile  Ala  Leu  Ala  Phe  Ala  Thr  Gly  Gly  Val  Leu  Val  Phe  Leu  Ala
CGT      GAC  AGG  TCA  ATT  GCT  ACG  TTT  CTT  GCG  GGA  GTT  GTT  TTG  CTC  TTC  CTT  TCG
Arg      Asp  Arg  Ser  Ile  Ala  Thr  Phe  Leu  Ala  Gly  Val  Val  Leu  Leu  Phe  Leu  Ser
***      **** **** **** **** **** **** **** **** **** **** **** **** **** **** **** **** ****
         Met       Met  Thr       Met            Val  Leu                 ATG       TTT       Ser
AGA      AAC  ACA  ATG  TCC  ATG  AGC  ATG  ATC  TTG  GGA  GTA  GTA  ATC  ATG  ATG  TTG  TCT
Arg      Asn  Thr  Met  Ser  Met  Ser  Met  Ile  Leu  Gly  Val  Val  Ile  Met  Met  Leu  Ser
***      **** **** **** **** **** **** **** **** **** **** **** **** **** **** **** **** ****
         Asn       Thr  Met  Ser  Met       Ile  Met  Val       Val  Leu  Val  Ile  Met  Met  Ser

         1510
ACC      AAT  GTG  CAT  GCT
Thr      Asn  Val  His  Ala
GTC      AAC  GTC  CAT  GCT
Val      Asn  Val  His  Ala
***      **** **** **** ****
CTA      GGA  GTT  GGG  GCG
Leu      Gly  Val  Gly  Ala
***      **** **** **** ****
```

FIG. 1i

```
                               10                      20                      30                      40                      50                      60
TTT AAT TGT CTG GGA ATG GGC AAT CGT GAC TTC ATA GAA GGA GCC AGT GGA GCC ACT TGG
Phe Asn Cys Leu Gly Met Gly Asn Arg Asp Phe Ile Glu Gly Ala Ser Gly Ala Thr Trp

                               70                      80                      90                     100                     110                     120
GTG GAC TTG GTG CTA GAA GGA GAT AGC TGC TTG ACA ATC ATG GCA AAC GAC AAA CCA ACA
Val Asp Leu Val Leu Glu Gly Asp Ser Cys Leu Thr Ile Met Ala Asn Asp Lys Pro Thr

                              130                     140                     150                     160                     170                     180
TTG GAC GTC CGC ATG ATT AAC ATC GAA GCT AGC CAA CTT GCT GAG GTC AGA AGT TAC TGC
Leu Asp Val Arg Met Ile Asn Ile Glu Ala Ser Gln Leu Ala Glu Val Arg Ser Tyr Cys

                              190                     200                     210                     220                     230                     240
TAT CAT GCT TCA GTC ACT GAC ATC TCG ACG GTG GCT CGG TGC CCC ACG ACT GGA GAA GCT
Tyr His Ala Ser Val Thr Asp Ile Ser Thr Val Ala Arg Cys Pro Thr Thr Gly Glu Ala
```

FIG. 2a

```
                250                 260                 270                 280                 290                 300
CAC AAC GAG AAG CGA GCT GAT AGT AGC TAT GTG TGC AAA CAA GGC TTC ACT GAT CGT GGG
His Asn Glu Lys Arg Ala Asp Ser Ser Tyr Val Cys Lys Gln Gly Phe Thr Asp Arg Gly

                310                 320                 330                 340                 350                 360
TGG GGC AAC GGA TGT GGA CTT TTC GGG AAG GGA AGC ATT GAC ACA TGT GCA AAA TTC TCC
Trp Gly Asn Gly Cys Gly Leu Phe Gly Lys Gly Ser Ile Asp Thr Cys Ala Lys Phe Ser

                370                 380                 390                 400                 410                 420
TGC ACC AGC AAA GCG ATT GGA AGA ACA ATC CAG CCA GAA AAC ATC AAA TAC GAA GTT GGC
Cys Thr Ser Lys Ala Ile Gly Arg Thr Ile Gln Pro Glu Asn Ile Lys Tyr Glu Val Gly

                430                 440                 450                 460                 470                 480
ATT TTT GTG CAT GGA ACC ACC ACT TCG GAA AAC CAT GGG AAT TAT TCA GCG CAA GTT GGG
Ile Phe Val His Gly Thr Thr Thr Ser Glu Asn His Gly Asn Tyr Ser Ala Gln Val Gly

                490                 500                 510                 520                 530                 540
GCG TCC CAG GCG GCA AAG TTT ACA ATA ACA CCC AAT GCT CCT TCG ATA ACC CTC GGG CTT
Ala Ser Gln Ala Ala Lys Phe Thr Ile Thr Pro Asn Ala Pro Ser Ile Thr Leu Gly Leu
```

FIG. 2b

```
                550                 560                 570                 580                 590                 600
GGT GAC TAC GGA GAA GTC ACG CTG GAC TGT GAG CCA AGG AGT GGA CTG AAC ACT GAA GCG
Gly Asp Tyr Gly Glu Val Thr Leu Asp Cys Glu Pro Arg Ser Gly Leu Asn Thr Glu Ala

                610                 620                 630                 640                 650                 660
TTT TAC GTC ATG ACC GTG GGG TCA AAG TCA TTT CTG GTC CAT AGG GAA TGG TTT CAT GAC
Phe Tyr Val Met Thr Val Gly Ser Lys Ser Phe Leu Val His Arg Glu Trp Phe His Asp

                670                 680                 690                 700                 710                 720
CTC GCT CTC CCC TGG ACG TCC CCT TCG AGC ACA GCG TGC AGA AAC AGA GAA CTC CTC ATG
Leu Ala Leu Pro Trp Thr Ser Pro Ser Ser Thr Ala Cys Arg Asn Arg Glu Leu Leu Met

                730                 740                 750                 760                 770                 780
GAA TTT GAA GAG GCG CAC GCC ACA AAA CAG TCC GTT GTT GCT CTT GGG TCA CAG GAA GGA
Glu Phe Glu Glu Ala His Ala Thr Lys Gln Ser Val Val Ala Leu Gly Ser Gln Glu Gly

                790                 800                 810                 820                 830                 840
GGC CTC CAT CAG GCG TTG GCA GGA GCC ATC GTG GTG GAG TAC TCA AGC TCA GTG AAG TTA
Gly Leu His Gln Ala Leu Ala Gly Ala Ile Val Val Glu Tyr Ser Ser Ser Val Lys Leu
```

FIG. 2c

```
                850                 860                 870                 880                 890                 900
ACA TCA GGC CAC CTG AAA TGT AGG ATG AAA ATG GAC AAA CTG GCT CTG AAA GGC ACA ACC
Thr Ser Gly His Leu Lys Cys Arg Met Lys Met Asp Lys Leu Ala Leu Lys Gly Thr Thr

                910                 920                 930                 940                 950                 960
TAT GGC ATG TGT ACA GAA AAA TTC TCG TTC GCG AAA AAT CCG GCG GAC ACT GGC CAC GGA
Tyr Gly Met Cys Thr Glu Lys Phe Ser Phe Ala Lys Asn Pro Ala Asp Thr Gly His Gly

                970                 980                 990                1000                1010                1020
ACA GTT GTC ATT GAA CTA TCC TAC TCT GGG AGT GAT GGC CCC TGC AAA ATT CCG ATT GTC
Thr Val Val Ile Glu Leu Ser Tyr Ser Gly Ser Asp Gly Pro Cys Lys Ile Pro Ile Val

               1030                1040                1050                1060                1070                1080
TCC GTT GCG AGC CTC AAT GAC ATG ACC CCC GTT GGG CGG CTG GTG ACA GTG AAC CCT TTC
Ser Val Ala Ser Leu Asn Asp Met Thr Pro Val Gly Arg Leu Val Thr Val Asn Pro Phe

               1090                1100                1110                1120                1130                1140
GTC GCG ACT TCC AGT GCC AAC TCA AAG CTG CTG GTC GAG ATG GAA CCC CCC TTC GGA GAC
Val Ala Thr Ser Ser Ala Asn Ser Lys Leu Leu Val Glu Met Glu Pro Pro Phe Gly Asp
```

FIG. 2d

```
                1150          1160          1170           1180           1190          1200
TCC TAC ATC GTG GTT GGG AGG GGA GAC AAG CAG ATC AAC CAC CAT TGG CAC AAA GCT GGA
Ser Tyr Ile Val Val Gly Arg Gly Asp Lys Gln Ile Asn His His Trp His Lys Ala Gly

                1210          1220          1230           1240           1250          1260
AGC ACG CTA GGC AAG GCC TTT TCA ACA ACT TTG AAG GGA GCT CAA AGA CTG GCA GCG TTG
Ser Thr Leu Gly Lys Ala Phe Ser Thr Thr Leu Lys Gly Ala Gln Arg Leu Ala Ala Leu

                1270          1280          1290           1300           1310          1320
GGC GAC ACA GCC TGG GAC TTT GGC TCC ATT GGA GGG GTC TTC AAC TCC ATA GGA AAA GCC
Gly Asp Thr Ala Trp Asp Phe Gly Ser Ile Gly Gly Val Phe Asn Ser Ile Gly Lys Ala

                1330          1340          1350           1360           1370          1380
GTT CAC CAA GTG TTT GGT GGT GCC TTC AGA ACA CTC TTT GGG GGA ATG TCT TGG ATC ACA
Val His Gln Val Phe Gly Gly Ala Phe Arg Thr Leu Phe Gly Gly Met Ser Trp Ile Thr

                1390          1400          1410           1420           1430          1440
CAA GGG CTA ATG GGT GCC CTA CTA CTC TGG ATG GGC GTC AAC GCA CGA GAC CGA TCA ATT
Gln Gly Leu Met Gly Ala Leu Leu Leu Trp Met Gly Val Asn Ala Arg Asp Arg Ser Ile
```

FIG. 2e

```
        1450                1460                1470                1480                1490                1500
GCT TTG GCC TTC TTA GCC ACA GGA GGT GTG CTC GTG TTC TTA GCG ACC AAT GTG CAT GCT
Ala Leu Ala Phe Leu Ala Thr Gly Gly Val Leu Val Phe Leu Ala Thr Asn Val His Ala
```

FIG. 2f

A DNA CODING FOR A FLAVIVIRUS ANTIGEN

This application is a continuation of application Ser. No. 07/809,255, filed Dec. 18, 1991, now abandoned, which is a continuation of Ser. No. 07/279,685, filed Dec. 5, 1988, now abandoned, which is a continuation in part of Ser. No. 06/932,419, filed Nov. 19, 1986, now U.S. Pat. No. 4,810, 492, issued Mar. 7, 1989.

This invention relates to a DNA coding for a flavivirus antigen. More particularly, the present invention is concerned with a DNA coding for an antigen which contains at least one epitope which is reactive to an anti-flavivirus antibody. The present invention also relates to a method for producing the antigen using the DNA. The antigen produced according to the method of the present invention has a high purity and can be used as a vaccine for Japanese encephalitis. Using the DNA of the present invention, the antigen can be safely produced on a large scale and at low cost by recombinant DNA technique. Further, due to its highly specific antigenicity, the antigen produced according to the present invention can be advantageously utilized as a diagnostic reagent for anti-flavivirus antibodies, and can also be utilized for the preparation of anti-flavivirus antibodies.

Japanese encephalitis (hereinafter often referred to as JE) is an infectious disease caused by the infection of the JE virus, and the mortality from the disease is high and the disease brings about heavy sequelae. In Japan, the number of patients suffering from JE has decreased notably in recent years. However, the disease sometimes prevails in East, Southeast and South Asia countries. This causes a social problem, which is not limited to areas where the disease prevails but develops into an international problem at the present day because there are many visit exchanges between the countries. The JE virus belongs to the genus Flavivirus of the family Togaviridae. According to virus taxonomy, about 50 viruses including JE virus belong to the genus Flavivirus. The viruses belonging to the genus Flavivirus are simply called flaviviruses. Until now, various studies have been made with respect to several flaviviruses, namely, JE virus, yellow fever virus, West Nile virus, dengue virus and the like. It is known that the structure of a flavivirus particle comprises three kinds of structural proteins, namely a glycoprotein E (sometimes called V3 antigen and having a molecular weight of about 53,000) which constitutes a main portion of the envelope of the flavivirus particle; a small protein M (sometimes called V1 antigen and having a molecular weight of about 8,700) which is present in the envelope; and a protein C (sometimes called V2 antigen and having a molecular weight of about 13,500) which constitutes the nucleocapsid of the flavivirus particle. In the flavivirus particle, there is a viral genome which comprises single-stranded RNA having a molecular weight of about $3.8\times10^6$ to about $4.2\times10^6$. The viral genome contains genes respectively coding for the above-mentioned three kinds of structural proteins. Of the above-mentioned three kinds of proteins, the protein E (hereinafter referred to as "V3 antigen") plays an important role in the initial step of virus infection. Therefore, it is expected to utilize the V3 antigen for the prevention or diagnosis of the infection of the virus. Various studies of the V3 antigen have been made. For example, the activity of the V3 antigen-neutralizing antiserum and the hemagglutinating activity, infected cells-fusing activity, hemolytic activity, etc. of the V3 antigen have been measured. There is a literature reporting that at least nine epitopes are present in the V3 antigen. Also it is known that the flaviviruses of different species have antigens which are closely related to or similar to one another.

Conventionally, the V3 antigen of JE virus has been produced as follows. Using a mouse brain or somatic cells derived from an animal as a culture host for culturing the virus, pathogenic seed viruses are cultured, and then all virus particles are separated from the culture. Subsequently, by a physico-chemical treatment, all of the separated virus particles are cleaved to obtain a mixture of V1, V2 and V3 antigens, virus RNA and the like, followed by isolation and purification of the V3 antigen. Such a conventional manner as mentioned above has the following disadvantages.

(1) The probability of biohazards is high because of the direct handling of pathogenic viruses.

(2) The production cost is high because the raw materials, production processes and equipments are very complicated.

(3) Highly purified V3 antigen is extremely difficult to obtain because there is a high possibility that the V3 antigen is contaminated with impurities derived from the culture host and culture medium.

The present inventors have made extensive and intensive studies to solve the above-mentioned problems. As a result, they have succeeded in cloning a cDNA which coding for the V3 antigen of JE virus which plays an important role in the infection of JE virus, and determining the base sequence of the cDNA which codes for the V3 antigen of JE virus. Furthermore, it has unexpectedly been found that when the cDNA is subjected to expression by the recombinant DNA technique, a protein (hereinafter referred to as "V3 protein") having an amino acid sequence corresponding to the V3 antigen of JE virus and having the same antigenicity as that of the JE virus can be obtained safely and stably on a large scale. Based on the above-mentioned novel findings, the present invention has been completed.

It is, therefore, an object of the present invention to provide a novel DNA coding for a flavivirus antigen which is extremely effective as a JE vaccine, which DNA is useful for producing the antigen safely on a large scale and at low cost.

The foregoing and other objects, features and advantages of the present invention will be apparent from the following detailed description taken in connection with the accompanying drawings.

BRIEF DESCRIPTION OF THE DRAWINGS

FIGS. 1*a* to 1*i* show the base sequences coding for V3 proteins of JE virus, yellow fever virus and West Nile virus and the amino acid sequences of V3 proteins of the above-mentioned viruses;

FIGS. 2*a* to 2*f* show the base sequence coding for V3 protein of JE virus (hereinafter often referred to as "JEV3 protein") (upper row) and the amino acid sequence of JEV3 protein (lower row);

In FIGS. 1*a* to 1*i*, the sequences are arranged in the following order from the top row through the bottom row:

Figure 3:
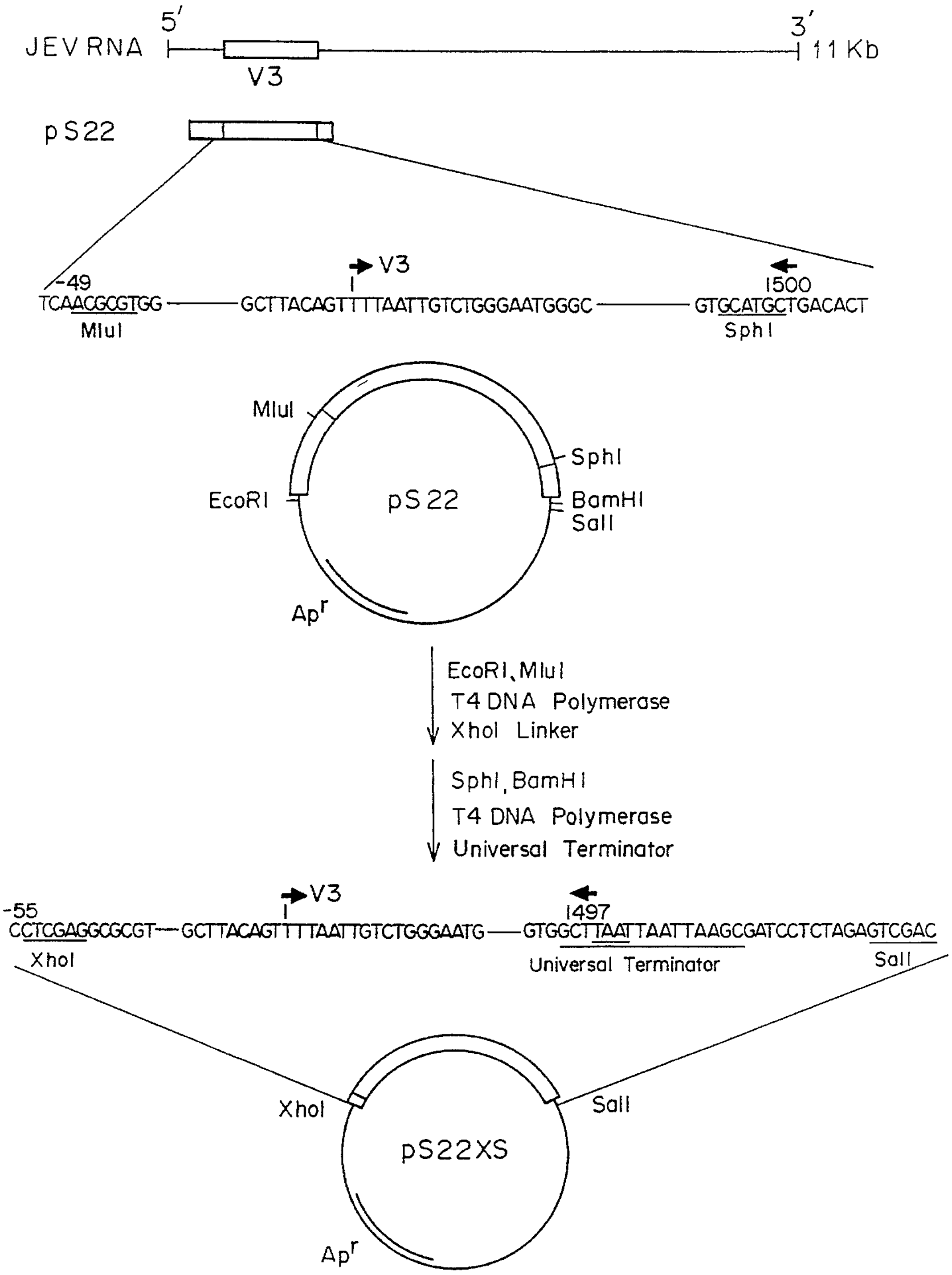
FIG. 3 shows a flow chart indicating the construction of pS22XS from pS22.

(1) base sequence coding for V3 protein of JE virus (2) amino acid sequence of V3 protein of JE virus deduced from the base sequence (1) mentioned above (3) base sequence coding for V3 protein of West Nile virus (4) amino acid sequence of V3 protein of West Nile virus deduced from the base sequence (3) mentioned above (5) base sequence coding for V3 protein of yellow fever virus (6) amino acid sequence of V3 protein of yellow fever virus deduced from the base sequence (5) mentioned above.

Further, in FIGS. *1a* to *1i*, the symbol "***" means that this portion in the base sequence or amino acid sequence is the same codon or amino acid as that of the base sequence or amino acid sequence of JEV3 protein at the corresponding portion; and the symbol " - - - " means that this portion in the base sequence or amino acid sequence is null, and therefore, two codons or amino acids adjacent to this symbol at its both sides are directly connected.

Essentially, according to the present invention, there is provided a deoxyribonucleic acid which comprises a base sequence coding for an antigen comprising at least part of an amino acid sequence represented by the following formula (I):

| | | | | | | | | | |
|---|---|---|---|---|---|---|---|---|---|
| Phe | Asn | Cys | Leu | Gly | Met | Gly | Asn | Arg | Asp |
| Phe | Ile | Glu | Gly | Ala | Ser | Gly | Ala | Thr | Trp |
| Val | Asp | Leu | Val | Leu | Glu | Gly | Asp | Ser | Cys |
| Leu | Thr | Ile | Met | Ala | Asn | Asp | Lys | Pro | Thr |
| Leu | Asp | Val | Arg | Met | Ile | Asn | Ile | Glu | Ala |
| Ser | Gln | Leu | Ala | Glu | Val | Arg | Ser | Tyr | Cys |
| Tyr | His | Ala | Ser | Val | Thr | Asp | Ile | Ser | Thr |
| Val | Ala | Arg | Cys | Pro | Thr | Thr | Gly | Glu | Ala |
| His | Asn | Glu | Lys | Arg | Ala | Asp | Ser | Ser | Tyr |
| Val | Cys | Lys | Gln | Gly | Phe | Thr | Asp | Arg | Gly |
| Trp | Gly | Asn | Gly | Cys | Gly | Leu | Phe | Gly | Lys |
| Gly | Ser | Ile | Asp | Thr | Cys | Ala | Lys | Phe | Ser |
| Cys | Thr | Ser | Lys | Ala | Ile | Gly | Arg | Thr | Ile |
| Gln | Pro | Glu | Asn | Ile | Lys | Tyr | Glu | Val | Gly |
| Ile | Phe | Val | His | Gly | Thr | Thr | Thr | Ser | Glu |
| Asn | His | Gly | Asn | Tyr | Ser | Ala | Gln | Val | Gly |
| Ala | Ser | Gln | Ala | Ala | Lys | Phe | Thr | Ile | Thr |
| Pro | Asn | Ala | Pro | Ser | Ile | Thr | Leu | Gly | Leu |
| Gly | Asp | Tyr | Gly | Glu | Val | Thr | Leu | Asp | Cys |
| Glu | Pro | Arg | Ser | Gly | Leu | Asn | Thr | Glu | Ala |
| Phe | Tyr | Val | Met | Thr | Val | Gly | Ser | Lys | Ser |
| Phe | Leu | Val | His | Arg | Glu | Trp | Phe | His | Asp |
| Leu | Ala | Leu | Pro | Trp | Thr | Ser | Pro | Ser | Ser |
| Thr | Ala | Cys | Arg | Asn | Arg | Glu | Leu | Leu | Met |
| Glu | Phe | Glu | Glu | Ala | His | Ala | Thr | Lys | Gln |
| Ser | Val | Val | Ala | Leu | Gly | Ser | Gln | Glu | Gly |
| Gly | Leu | His | Gln | Ala | Leu | Ala | Gly | Ala | Ile |
| Val | Val | Glu | Tyr | Ser | Ser | Ser | Val | Lys | Leu |
| Thr | Ser | Gly | His | Leu | Lys | Cys | Arg | Met | Lys |
| Met | Asp | Lys | Leu | Ala | Leu | Lys | Gly | Thr | Thr |
| Tyr | Gly | Met | Cys | Thr | Glu | Lys | Phe | Ser | Phe |
| Ala | Lys | Asn | Pro | Ala | Asp | Thr | Gly | His | Gly |
| Thr | Val | Val | Ile | Glu | Leu | Ser | Tyr | Ser | Gly |
| Ser | Asp | Gly | Pro | Cys | Lys | Ile | Pro | Ile | Val |
| Ser | Val | Ala | Ser | Leu | Asn | Asp | Met | Thr | Pro |
| Val | Gly | Arg | Leu | Val | Thr | Val | Asn | Pro | Phe |
| Val | Ala | Thr | Ser | Ser | Ala | Asn | Ser | Lys | Leu |
| Leu | Val | Glu | Met | Glu | Pro | Pro | Phe | Gly | Asp |
| Ser | Tyr | Ile | Val | Val | Gly | Arg | Gly | Asp | Lys |
| Gln | Ile | Asn | His | His | Trp | His | Lys | Ala | Gly |
| Ser | Thr | Leu | Gly | Lys | Ala | Phe | Ser | Thr | Thr |
| Leu | Lys | Gly | Ala | Gln | Arg | Leu | Ala | Ala | Leu |
| Gly | Asp | Thr | Ala | Trp | Asp | Phe | Gly | Ser | Ile |
| Gly | Gly | Val | Phe | Asn | Ser | Ile | Gly | Lys | Ala |
| Val | His | Gln | Val | Phe | Gly | Gly | Ala | Phe | Arg |
| Thr | Leu | Phe | Gly | Gly | Met | Ser | Trp | Ile | Thr |
| Gln | Gly | Leu | Met | Gly | Ala | Leu | Leu | Leu | Trp |

-continued

| | | | | | | | | | |
|---|---|---|---|---|---|---|---|---|---|
| Met | Gly | Val | Asn | Ala | Arg | Asp | Arg | Ser | Ile |
| Ala | Leu | Ala | Phe | Leu | Ala | Thr | Gly | Gly | Val |
| Leu | Val | Phe | Leu | Ala | Thr | Asn | Val | His | Ala |
| ..... (I) | | | | | | | | | |

wherein Ala stands for an alanine residue, Arg an arginine residue, Asn an asparagine residue, Asp an aspartic acid residue, Cys a cysteine residue, Gln a glutamine residue, Glu a glutamic acid residue, Gly a glycine residue, His a histidine residue, Ile an isoleucine residue, Lys a lysine residue, Leu a leucine residue, Met a methionine residue, Phe a phenylalanine residue, Pro a proline residue, Ser a serine residue, Thr a threonine residue, Trp a tryptophan residue, Tyr a tyrosine residue, and Val a valine residue, said part containing at least one epitope which is reactive to an anti-flavivirus antibody.

Further, according to the present invention, there is provided a process for producing an antigen comprising at least part of an amino acid sequence represented by the above-mentioned formula (I), said part containing at least one epitope which is reactive to an anti-flavivirus antibody, which comprises:

(a) ligating a deoxyribonucleic acid comprising a base sequence coding for said antigen to a replicable expression vector to obtain a replicable recombinant DNA comprising said deoxyribonucleic acid and said replicable expression vector;

(b) transforming cells of a microorganism or cell culture with said replicable recombinant DNA to form transformants;

(c) selecting said transformants from parent cells of the microorganism or cell culture;

(d) incubating said transformants, causing said transformants to express said deoxyribonucleic acid and produce an antigen; and (e) isolating said antigen from the incubated transformants.

The antigen encoded by the DNA of the present invention comprises at least part of an amino acid sequence represented by the above-mentioned formula (I). The amino acid sequence of the formula (I) corresponds to the full amino acid sequence of the V3 antigen of JE virus. The present antigen may comprise the whole amino acid sequence of the formula (I). The antigen having the whole amino acid sequence of the formula (I) is hereinafter referred to as JEV3 protein. Alternatively, the present antigen may comprise a part of the amino acid sequence of the formula (I) insofar as the part contains at least one epitope which is reactive to an anti-flavivirus antibody.

The "epitope" is an antigenic determinant, which means a structure in an antigen which determines the specificity of antigen-antibody reaction.

As the part of the amino acid sequence of the formula (I), there may be mentioned, for example, a part corresponding to the amino acid sequence of from 45th to 159th amino acids counted from the N-terminus of the amino acid sequence of the formula (I), a part corresponding to the amino acid sequence of from 375th to 456th amino acids counted from the N-terminus of the amino acid sequence of the formula (I), etc.

The antigen encoded by the DNA of the present invention having the amino acid sequence of the formula (I) (i.e. JEV3 protein) may be prepared by a process comprising steps (1) to (9) as mentioned below.

In the step (1), a genomic RNA is extracted from JE virus. In this step, conventional customary techniques such as phenol extraction technique and the like may be used.

In the step (2), a double-stranded cDNA complementary to the virus RNA obtained in the step (1) is prepared. In this step, there may be employed a conventional customary method in which a reverse transcriptase is used.

In the step (3), the cDNA is cloned and the base sequence of the cloned cDNA is determined. As a vector for the cloning, there may be used any of known vectors such as plasmids, having adaptability to a prokaryotic cell such as *Escherichia coli, Bacillus subtilis* and the like and vectors derived from bacteriophages such as phage, T4 phages and the like. In this step, it is desirable that a suitable combination of a cloning vector and a host cell be selected.

In the step (4), a cloned cDNA containing a gene coding for JEV3 protein (hereinafter referred to as "JEV3 gene") is identified.

Usually, structural genes derived from cells have a specific· base sequence in the region of the initiation and termination of translation, and the regulator genes are analogous in structure. Hence, it is relatively easy to detect and identify the regions of such structural genes. On the other hand, in the case of JEV3 gene, since the regions of the initiation and termination of translation and the regulator genes are not present, there are no specific base sequences usable as an index and, hence, the detection and identification of the regions of JEV3 gene are extremely difficult. Such difficulty, however, has been skillfully overcome by the present inventors. That is, the present inventors analyzed the base sequence of cloned cDNA, expressed the cloned cDNA and effected the immunological detection and identification of the expressed product, and further, they compared the base sequence of the cloned cDNA with the already reported amino acid sequence of V3 proteins and base sequence of genes with respect to V3 genes of the yellow fever virus and West Nile virus, thereby to determine the base sequence of the cDNA of JEV3 gene.

As a result, it was found that the JEV3 gene has a base sequence of the following formula (II):

TTT AAT TGT CTG GGA ATG GGC AAT CGT GAC
TTC ATA GAA GGA GCC AGT GGA GCC ACT TGG
GTG GAC TTG GTG CTA GAA 9GA GAT AGC TGC
TTG ACA ATC ATG GCA AAC GAC AAA CCA ACA
TTG GAC GTC CGC ATG ATT AAC ATC GAA GCT
AGC CAA CTT GCT GAG GTC AGA AGT TAC TGC
TAT CAT GCT TCA GTC ACT GAC ATC TCG ACG
GTG GCT CGG TGC CCC ACG ACT GGA GAA GCT
CAC AAC GAG AAG CGA GCT GAT AGT AGC TAT
GTG TGC AAA CAA GGC TTC ACT GAT CGT GGG
TGG GGC AAC GGA TGT GGA CTT TTC GGG AAG
GGA AGC ATT GAC ACA TGT GCA AAA TTC TCC
TGC ACC AGC AAA GCG ATT GGA AGA ACA ATC
CAG CCA GAA AAC ATC AAA TAC GAA GTT GCC
ATT TTT GTG CAT GGA ACC ACC ACT TCG GAA
AAC CAT GGG AAT TAT TCA GCG CAA GTT GGG
GCG TCC CAG GCG GCA AAG TTT ACA ATA ACA
CCC AAT CGT CCT TCG ATA ACC CTC GGG CTT
GGT GAC TAC GGA GAA GTC ACG CTG GAC TGT
GAG CCA AGG AGT GGA CTG AAC ACT GAA GCG
TTT TAC GTC ATG ACC GTG GGG TCA AAG TCA
TTT CTG GTC CAT AGG GAA TGG TTT CAT GAC
CTC GCT CTC CCC TGG ACG TCC CCT TCG AGC
ACA GCG TGC AGA AAC AGA GAA CTC CTC ATG
GAA TTT GAA GAG GCG CAC GCC ACA AAA CAG
TCC GTT GTT GCT CTT GGG TCA CAG GAA GGA
GGC CTC CAT CAG GCG TTG GCA GGA GCC ATC
GTG GTG GAG TAC TCA AGC TCA GTG AAG TTA

-continued

ACA TCA GGC CAC CTG AAA TGT AGG ATG AAA
ATG GAC AAA CTG GCT CTG AAA GGC ACA ACC
TAT GGC ATG TGT ACA GAA AAA TTC TCG TTC
GCG AAA AAT CCG GCG GAC ACT GGC CAC GGA
ACA GTT GTC ATT GAA CTA TCC TAC TCT GGG
AGT GAT GGC CCC TGC AAA ATT CCG ATT GTC
TCC GTT GCG AGC CTC AAT GAC ATG ACC CCC
GTT GGG CGG CTG GTG ACA GTG AAC CCT TTC
GTC GCG ACT TCC AGT GCC AAC TCA AAG CTG
CTG GTC GAG ATG GAA CCC CCC TTC GGA GAC
TCC TAC ATC GTG GTT GGG AGG GGA GAC AAG
CAG ATC AAC CAC CAT TGG CAC AAA GCT GGA
AGC ACG CTA GGC AAG GCC TTT TCA ACA ACT
TTG AAG GGA GCT CAA AGA CTG GCA GCG TTG
GGC GAC ACA GCC TGG GAC TTT GGC TCC ATT
GGA GGG GTC TTC AAC TCC ATA GGA AAA GCC
GTT CAC CAA GTG TTT GGT GGT GCC TTC AGA
ACA CTC TTT GGG GGA ATG TCT TGG ATC ACA
CAA GGG CTA ATG GGT GCC CTA CTA CTC TGG
ATG GGC GTC AAC GCA CGA GAC CGA TCA ATT
GCT TTG GCC TTC TTA GCC ACA GGA GGT GTG
CTC GTG TTC TTA GCG ACC AAT GTG CAT GCT
..... (II)

wherein A represents a deoxyadenylic acid residue, G a deoxyguanylic acid residue, C a deoxycytidylic acid residue and T a deoxythymidylic acid residue, and the left and right ends of formula(II) represent the 5'-hydroxyl group side and 3'-hydroxyl group side, respectively.

In accordance with degeneracy of genetic code, it is possible to substitute at least one base of the base sequence of a gene by another kind of base without causing the amino acid sequence of the polypeptide produced from the gene to be changed. Hence, the DNA coding for JEV3 protein may also have any base sequence that has been changed by substitution in accordance with degeneracy of genetic code. In this instance, the amino acid sequence deduced from the base sequence obtained by the above-mentioned substitution is identical with the amino acid sequence of the formula (I) as defined before.

In the step (5), the cDNA of JEV3 gene is ligated to a replicable expression vector.

In this step, the cDNA of JEV3 gene is prepared from the cloned cDNA obtained in the step (4) and ligated to a replicable expression vector to form a replicable recombinant DNA. As a replicable expression vector used in this step, there may be mentioned any known vectors such as expression plasmids, expression shuttle vectors and expression vectors derived from viruses such as vaccinia virus and SV40, which have adaptability to host cells to be used. With respect to the host cells, an explanation will be given later.

The ligation of the cDNA of JEV3 gene to a replicable expression vector may be effected by a customary method. In practicing the ligation, it should be noted that since the cDNA of JEV3 gene does not have regions for the initiation and termination of translation, it is necessary for the cDNA to be supplemented by DNAs which have base sequences corresponding to such regions. In this connection, in the case where the expression vector to be ligated to the cDNA contains base sequences corresponding to such regions, the cDNA is ligated to the expression vector in such a manner that the cDNA can be expressed utilizing such regions. On the other hand, in the case where the expression vector to be ligated to the cDNA does not contain the regions for initiation and termination for translation, the cDNA is supplemented by DNAs which have base sequences corresponding to such regions and ligated to an expression vector.

Further, an expression vector to which the cDNA of JEV3 gene is to be ligated may be modified in order that:

(1) the antigenicity and immunogenicity of an expressed product (JEV3 protein) are enhanced;

(2) the stability of the cDNA of JEV3 gene in an expression vector and in a host cell is in creased;

(3) the yield of the JEV3 protein produced by gene expression is increased; and (4) the JEV3 antigen produced by gene expression in a host cell is secreted out of the host cell so that the extraction and purification of the antigen is simplified.

Furthermore, in effecting the ligation of the cDNA of JEV3 gene to an expression vector, if desired, the cDNA of JEV3 gene may be ligated to the expression vector through a suitable linker.

The cloned cDNA obtained in the above step (4) sometimes contains, in addition to the base sequence coding for JEV3 protein, a base sequence derived from the other gene of the JE virus than JEV3 gene. In such a case, the base sequence other than that coding for JEV3 protein may be deleted from the cDNA before ligation. Alternatively, the cDNA as such may be used.

In the step (6), the replicable recombinant DNA containing the cDNA of JEV3 gene is transferred into a host cell to obtain a transformant.

In this step, transformation of a host cell with the recombinant DNA is effected by a customary method. As examples of the host cells, there may be mentioned prokaryotic cells such as *Escherichia coli* and *Bacillus subtilis,* and eukaryotic cells such as a yeast and a higher organism cell culture.

The transformants formed by the transformation are selected from parent cells which remain untransformed with the recombinant DNA using as a criterion, for example, a phenotypical trait such as drug resistance imparted by the replicable expression vector having gene for the phenotypical trait.

In the step (7), the transformant is cultured to express the cDNA of JEV3 gene and produce the JEV3 protein.

In the step (8), the present antigen produced by expression is isolated from the incubated transformant by customary extraction and purification methods.

In this step, conventional techniques may be used in combination. For example, techniques such as filtration, salting-out, centrifugation and column chromatography may be used in combination for extracting and purifying the present antigen.

Thus, there is obtained a flavivirus antigen comprising an amino acid sequence represented by the above-mentioned formula (I) in substantially pure form.

In the step (9), the antigenicity and immunogenicity of the present antigen are assayed.

In this step, conventional techniques may be used in combination. For example, techniques such as an enzyme-linked immunosorbent assay (hereinafter referred to as "ELISA") and neutralization test (50% plaque reduction method: "Standard for the biological preparation of medicines", p. 76, supervised by Pharmaceutical and Supply Bureau, Ministry of Health and Welfare, Japan, and issued by the Association of Bacterial Pharmaceutical Preparation on October 10, 1985) may be used in combination for assaying the antigenicity and immunogenicity.

As described above, the JEV3 protein is prepared by means of recombinant DNA technique using the cDNA of JEV3 gene having the base sequence represented by the formula (II). In the above-mentioned method, the cDNA of JEV3 gene is obtained from the JE virus through cloning. Alternatively, the cDNA of JEV3 gene may be organo-chemically synthesized using a commercially available automatic DNA synthesizer etc.

In the case where the antigen of the present invention comprises part of the JEV3 protein which part contains at least one epitope that is reactive to an anti-flavivirus antibody, such an antigen may be produced by means of recombinant DNA technique in substantially the same manner as described in the above Step (5) to (8) except that instead of the cDNA of JEV3 gene, a portion of the cDNA of JEV3 gene corresponding to the above-mentioned part of the JEV3 protein is ligated to an expression vector. The part of the JEV3 gene may be prepared by cleaving the cDNA of JEV3 gene using, for example, an appropriate restriction enzyme etc. Alternatively, the part of the cDNA of JEV3 gene may be organo-chemically synthesized using a commercially available automatic DNA synthesizer.

As mentioned above, the antigen encoded by the DNA of the present invention may be produced by gene expression. The antigen may also be obtained in the form of a fused peptide comprising a part or whole of the amino acid sequence of the JEV3 protein and, attached thereto at its C-terminus and/or N-terminus, the amino acid sequence of other peptide such as a peptide derived from a linker, peptide derived from an expression vector and/or peptide derived from the other structural protein of the flavivirus than the JEV3 protein. In this case, the fused peptide may be cleaved chemically or enzymatically to separate into the part or whole of the amino acid sequence of JEV3 protein and the amino acid sequence of the other peptide which has been attached thereto. Alternatively, the fused peptide as such may be used as an antigen if the antigenicity and immunogenicity are not affected by the presence of the other peptide than the JEV3 protein.

The antigen may also be organo-chemically synthesized using a commercially available automatic peptide synthesizer etc. Further, the redesigning and modification of each epitope of the antigen of the present invention may be readily effected according to a known customary method of protein engineering.

The antigen encoded by the DNA of the present invention may be used as an active ingredient of flavivirus vaccines, especially JE vaccine.

The vaccine may be prepared by adding the antigen encoded by the DNA of the present invention to a sterilized isotonic solution such as physiological saline or phosphate buffer. In this case, it is preferred that a peptone, amino acid, saccharide or the like be incorporated as a stabilizer in the vaccine. The vaccine thus obtained is in a liquid form. But the vaccine may be reformulated into a precipitated vaccine by adding an adjuvant for enhancing immunogenicity, or into a lyophilized vaccine which is highly stable and convenient for transportation. Further, the immunogenicity of the antigen may be enhanced by introducing a saccharide chain to the antigen by means of the molecular fusion technique or by modification in the cell after the translation.

The vaccine containing the present antigen may generally be administered in the form of a liquid or suspension. Therefore, in the case where the vaccine is a lyophilized vaccine, the vaccine is dissolved or suspended in the above-mentioned sterilized isotonic solution before administration. The concentration of the present antigen in the vaccine for administration may generally be about 0.001 to 1000 μg/ml. Generally, the vaccine may be administered subcutaneously or intramuscularly. The dose of the vaccine per adult may generally be in the range of from 0.1 to 2.0 ml. In general, the dose of the vaccine per child may be half as much as that of the vaccine per adult. The vaccine may generally be administered twice at an interval of about one week to one month and then, about one year later, administered once more.

Further, the antigen encoded by the DNA the present invention may be used as an immunological diagnostic for detecting infection from JE virus. The present antigen may also be used as an immunological diagnostic for detecting infection from flaviviruses other than JE virus which have an antigenicity which is closely related to or similar to that of the antigen encoded by the DNA of the present invention. For example, the antigen of the present substance is useful for use in ELISA, hemagglutination test, passive hemagglutination test, complement fixation test and other various tests in which an antigen or antibody labelled with a fluorescent pigment, an enzyme, a radioisotope, etc. are respectively used.

The antigen encoded by the DNA of the present invention may be used for detecting and identifying a flavivirus antibody according to the above-mentioned various test methods.

The antigen encoded by the DNA of the present invention may also be used for producing an antibody against the present antigen. The thus produced antibody may be advantageously used for detecting and identifying a flavivirus antigen according to the above-mentioned test methods. The production of such an antibody may be effected by a method in which the antigen encoded by the DNA of the present invention is injected into a laboratory animal, thereby to cause the animal to produce an antibody and then the blood or body fluid of the animal is collected. The antibody may also be produced by means of a customary cell fusion technique. When the antibody is produced by the former method, there is obtained a polyclonal antibody. On the other hand, when the antibody is produced by the latter method, there is obtained a monoclonal antibody.

Furthermore, the antigen encoded by the DNA of the present invention or the antibody against the present antigen may be used as a bioseparator, bioreactor and biosensor utilizing the antigen-antibody reaction. In this case, the antigen or the antibody against the present antigen may be fixed onto a substrate or support according to the known customary method. In accordance with the purpose, the antigen and the antibody against the present antigen may be labelled with a fluorescent pigment, an enzyme, a radioisotope or the like according to the known customary method.

The DNA of the present invention coding for the above-mentioned antigen has the following advantages.

By the use of the present DNA, the above-mentioned antigen can be produced by recombinant DNA technique. The molecular structure of the thus produced antigen is clear. Hence, by the use of the antigen, it is possible to provide highly effective, highly safe, uniform biological preparations and highly specific, highly effective diagnostics. Further, as mentioned above, the antigen is not produced by the infection of an animal with a virus, but produced by gene expression of the DNA of the present invention in a host cell. Hence, the possibility of bio-hazard during the steps of production of the antigen is substantially eliminated. Also, the production cost can be decreased. Moreover, since all of the materials, e.g. medium, of the incubation system are known in respect of the composition and construction thereof, purification is facile and an antigen product having a high purity can be obtained.

The present invention will now be described in detail with reference to the following Examples, which should not be construed to be limiting the scope of the present invention.

EXAMPLE 1

Step 1 [Extraction of the genomic RNA of Japanese encephalitis virus]

JE virus strain JaOArS982 was cultured using, as a culture host, cells of a cell line C6/36 derived from *Aedes albopictus,* a kind of mosquito (Igarashi, A., J. Gen. Virol., 40, 531, 1973) in a nutrient culture medium at 28° C. for 48 hours. After culturing, a supernatant of the culture medium was collected. Then, to the supernatant were added 6 g/dl of polyethylene glycol 6000 and 2.22 g/dl of sodium chloride and the obtained mixture was stirred for 15 min. The mixture was subjected to centrifugation at 12,000 g for 30 min to precipitate virus particles. The virus particles were collected and suspended in STE buffer (0.1M NaCl, 0.01M Tris-HCl and 0,001M EDTA, pH 7.6). The thus obtained suspension was layered over 15% sucrose solution in a centrifuge tube and subjected to centrifugation at 37,000 rpm for 120 min to obtain precipitates. The resultant precipitates were dissolved in STE-0.1% SDS (sodium dodecyl sulfate). Then, to the obtained solution was added the same volume of STE-saturated phenol for the purpose of extracting the genomic RNA of the virus and the resulting mixture was thoroughly stirred. The aqueous layer of the mixture was taken out and ethanol was added to the aqueous layer in a volume 2 times that of the aqueous layer. The thus obtained mixture was allowed to stand one night at −20° C. and subjected to centrifugation at 15,000 rpm for 30 min to precipitate RNA. The precipitated RNA was collected and lyophilized, and then suspended in STE-0.1% SDS. The resulting suspension was layered over a sucrose solution in a centrifuge tube which sucrose solution contained 0.01% SDS and had a density gradient of 15 to 30% (w/w) and subjected to centrifugation at 45,000 rpm for 180 min. A fraction having a sedimentation constant of 42S was collected from the centrifuge tube and pooled, and subjected to precipitation using ethanol to obtain precipitates. The precipitates were dried and dissolved in 50 mM Tris-HCl (pH 7.9) to obtain a purified virus RNA solution.

Step 2 [Preparation of a double-stranded cDNA containing a DNA which is complementary to the genomic RNA]

To 50 μl of the virus RNA solution containing 10 μg of the genomic RNA were added 10 mM $MgCl_2$, 250 mM NaCl, 2.5 mM $MnCl_2$, 0.5 mg/ml bovine serum albumin (hereinafter often referred to as "BSA"), 1 mM ATP, 30 units of RNase inhibitor and 1 unit of poly(A) polymerase, and the resulting mixture was incubated at 37° C. for 5 min. Then, the mixture was subjected to extraction by phenol and precipitation by ethanol to precipitate RNA, followed by centrifugation to obtain precipitates. The precipitates were dried to obtain a dried RNA. Subsequently, the obtained RNA was dissolved in 50 μl of a solution containing 0.1M KCl, 10 mM $MgCl_2$, 10 mM DTT, 1 mM dNTP, 20 μg of oligo$(dT)_{12-18}$, 50 mM Tris-HCl (pH 7.9) and 30 units of reverse transcriptase, and the resulting mixture was subjected to incubation at 42° C. for 60 min. To the mixture was added 150 μl of an enzyme solution containing 0.1 mM $MgSO_4$, 0.5 mg/ml BSA, 1 mM dNTP, 100 μM NAD, 0.5M Tris-HCl (pH 7.9), 25 units of RNase H, 1 unit of DNA ligase and 20 units of DNA polymerase I to obtain 200 μl of a mixture. The mixture was subjected to incubation at 15° C. for 2 hours. The resulting reaction mixture was subjected to phenol extraction and ethanol precipitation to obtain precipitates. Then, the precipitates were dissolved in 100 μl of an aqueous solution containing of 10 mM $MgCl_2$, 50 mM NaCl, 0.1 mg/ml BSA, 1 mM DTT, 1 mM dNTP and 50 mM Tris-HCl (pH 7.9). To the resulting solution was added 2 units of T4DNA polymerase and the resulting mixture was incubated at 37° C. for 10 min. After incubation, the mixture was subjected to phenol extraction and ethanol precipitation to obtain a double-stranded cDNA containing a DNA which is complementary to the viral genomic RNA.

Step 3 [Cloning of the cDNA and determination of the base sequence thereof]

The double-stranded cDNA obtained in Step 2 was dissolved in an aqueous solution containing 60 mM Tris-HCl (pH 7.6), 6.6 mM $MgCl_2$, 10 mM DTT and 1 mM ATP. To the thus obtained solution were added a BamHI linker and T4DNA ligase, followed by incubation at 4° C. for 16 hours to advance a ligation reaction of the cDNA with the linker. Thereafter, the BamHI linker remaining unreacted was removed by effecting a gel filtration using CL-4B gel which had been equilibrated with $TEN^{50}$ buffer consisting of 10 mM Tris-HCl (pH 8.0), 50 mM NaCl and 1 mM EDTA. Then, the linker which had been ligated to the cDNA in excess was removed by digesting the linker with BamHI and effecting a gel filtration using CL-4B gel. Thus, there was prepared a double-stranded cDNA to both ends of which BamHI linker was ligated. The thus obtained cDNA was inserted into the BamHI site of a cloning vector pUC13 (manufactured and sold by Pharmacia Fine Chemicals AB, Sweden). Illustratively stated, pUC13 was cleaved by BamHI. The cDNA to both ends of which a BamHI linker was ligated was added to the cleaved pUC13 and the resulting mixture was reacted in the presence of T4DNA ligase at 4° C. for 16 hours to ligate the cDNA with the vector pUC13. Then, the resulting ligation product, i.e. recombinant DNA, was transferred into a cell of *Escherichia coli* strain DH1 (ATCC No. 33849) to obtain a transformant. Subsequently, the cDNA fragments having various lengths were prepared from the cDNA as follows. First, the cDNA was prepared from the above-mentioned transformant and dissolved in 100 μl of a Bal31 buffer consisting of 50 mM Tris-HCl (pH 8.0), 12 mM $CaCl_2$, 12 mM $MgCl_2$ and 400 mM NaCl. To the resulting solution was added 2 units of exonuclease Bal31, followed by incubation at 20° C. At each point of time of 3, 6, 10 and 15 min after the incubation, 20 μl of the reaction mixture was collected and subjected to phenol extraction and ethanol precipitation, thereby to obtain cDNA fragments. Then, the cDNA fragments were dissolved in a T4DNA polymerase buffer containing 70 m M Tris-HCl (pH 7.5), 10 mM $MgCl_2$, 5 mM dithiothreitol and 200 μM dNTP, and T4 DNA polymerase was added to the obtained solution. The resulting mixture was incubated at 37° C. for 30 min to convert both ends of each of the cDNA fragments into blunt ends. Subsequently, the cDNA fragments were separately inserted into a HincII site of cloning vector pUC19 (manufactured and sold by Pharmacia Fine Chemicals AB, Sweden) to form recombinant vectors. The recombinant vectors were separately transferred into *E. coli* strain JM83 to obtain transformants containing various sizes of the cDNA fragments. The transformants were separately cultured to obtain the cDNA fragment clones. The base sequences of the obtained clones were determined by dideoxy chain termination method (Sanger, F. et al., Proc. Natl. Acad. Sci. USA., 74, 5463, 1977; and Hattori, M. et al., Anal. Biol., 152, 232, 1986). As a result, it was found that one of the clones was a cDNA consisting of about 4000 base pairs (hereinafter referred to as "bp") which corresponds to a partial base sequence of the genomic RNA of the JE virus, said partial base sequence starting from the site about 2000 bp downstream of the 5'-end of the genomic RNA and extending to a position such as to have about 4000 base pairs. This clone was designated K68. The clone K68 was found to contain a base sequence corresponding to part of the V3 gene of JE virus but not a full sequence of the V3 gene. Then, an oligonucleotide (26 mer) having the following base sequence complementary to part of V3 gene in the genomic RNA of the JE virus and contained in the sequence of the clone K68 was organo-chemically synthesized: dGTACGGCTTCCCACATTTGGTGCTCC, 26mer.

Step 4 [Cloning of clone S22 containing a DNA region coding for V3 protein]

Substantially the same procedures as in Step 2 except that the oligonucleotide (26 mer) prepared in Step 3 was used as a primer for cDNA synthesis were repeated to obtain cDNAs. The thus obtained cDNAs were separately inserted in a cloning vector pUC13 to obtain recombinant vectors and the recombinant vectors were separately transferred into the above-mentioned *E. coli* strain to form transformants. From each transformant, recombinant vector was isolated by an alkali extraction method [Nucleic Acid Res., 7 (6), 1513–1523 (1979)] and subjected to determination of the base sequence by the method as described in Step 3. As a result, it was found that one of the recombinant vectors contained a cDNA fragment having a molecular length of about 2500 bp which cDNA fragment corresponds to a partial base sequence of the genomic RNA of the JE virus, said partial sequence starting from the 5'-end of the genomic RNA and extending to a position such as to have about 2500 bp. The cDNA fragment is designated clone S22. The base sequence of the clone S22 and the amino acid sequence coded for by the base sequence were compared with the base sequences of the genomic RNA of two flaviviruses other than JE virus, i.e., yellow fever virus and West Nile virus and the amino acid sequence coded for by the genomic RNA, which sequences are described in Rice, C. M. et al, Science, 229, 726, 1985 and Wengler, G et al Virology, 147, 264, 1985. As a result, it was found that the clone S22 contained the DNA region coding for V3 protein of Japanese encephalitis virus.

The results are shown in FIGS. 2*a* to 2*f*. The recombinant vector carrying the clone S22 was designated plasmid pS22 (see FIG. 3). The *Escherichia coli* containing the recombinant vector carrying the clone S22 obtained above was designated *E. coli* strain JM83/pS22 and deposited at the Fermentation Research Institute under the Accession No. FERM-BP 1074.

Step 5 [Construction of an expression plasmid carrying a V3 protein gene]

The plasmid pS22 carrying the DNA fragment clone S22 has an MluI site at 49 bp upstream of the 5'-end of the V3 protein gene, and has an SphI site at 7 bp upstream of the 3'-end of the gene. The plasmid of pS22 was separated from *E. coli* strain JM83/pS22 in substantially the same manner as described in Step 4 and dissolved in a solution containing 10 mM Tris-HCl (pH 7.5), 100 mM NaCl and 7 mM $MgCl_2$. To the thus obtained solution were added restriction enzymes MluI and EcoRI, followed by incubation at 37° C. for 2 hours to cleave two sites, i.e. the MluI site and the EcoRI site of the plasmid, which EcoRI site was located further upstream of the 5'-end of the V3 protein gene than the MluI site. After the cleavage, the mixture was subjected to phenol extraction and ethanol precipitation to recover a DNA. The DNA was dissolved in the above-mentioned T4DNA polymerase buffer and heated at 37° C. for 30 min to convert both ends of the DNA into blunt ends, The resulting mixture was subjected to phenol extraction and ethanol precipitation to recover a DNA. An XhoI linker was ligated to each of both ends of the DNA in substantially the same manner as described in Step 3. *E. coli* strain JM83 was transformed with the linker-ligated DNA to obtain a transformant. By culturing the transformant, the linker-ligated DNA was cloned. The cloned linker-ligated DNA was designated S22X (see FIG. 3). The plasmid carrying the S22X was designated plasmid pS22X.

The plasmid pS22X carrying the clone S22X was dissolved in a solution containing 10 mM Tris-HCl (pH 7.5), 100 mM NaCl and 7 mM $MgCl_2$, and digested with restriction enzymes SphI and BamHI at 37° C. for 2 hours. Recovery of a DNA and converting of both ends of the DNA into blunt ends by the use of the T4 DNA polymerase were carried out in substantially the same manner as described above. Universal terminator (manufactured and sold by Pharmacia Fine Chemicals Co., Sweden) was ligated to the DNA, and the terminator-ligated DNA was used to transform *E. coli* strain JM83. The above-obtained DNA was designated clone S22XS (see Fig. 1).

On the other hand, as the expression vector, use was made of vector YEp133PCT. This vector was constructed by the present inventors as follows. First, with respect to the plasmid YEp13 (ATCC Accession No. 37115), the LEU2 gene fragment thereof obtained by cleavage with the XhoI and SalI of the plasmid was re-ligated to the remaining plasmid fragment in a reverse direction to cause the XhoI and SalI sites at both ends of the gene fragment to disappear. Second, the BamHI-SalI fragment present in the $Tc^r$ gene of the plasmid was replaced by a BamHI-SalI fragment of about 650 bp in length containing the PHO5 promoter derived from pPHO5 (see Kenji Arima et al., Nucl. Acid Res. 11, 1657, 1983). Third, the above-replaced BamHI-SalI fragment was trimmed from the SalI site thereof to the 3'-end of the promoter contained therein by the use of exonuclease Bal31. Fourth, an XhoI linker was inserted into the promoter at the 3' end thereof to incorporate a cloning site. Fifth, a DNA fragment of about 800 bp in length prepared by ligating XhoI and SalI linkers, at the HindIII and EcoRI sites, respectively, to the HindIII-EcoRI fragment containing a TRP1 terminator and an ARS (autonomous replication sequence) which HindIII-EcoRI fragment was obtained from YRp7 (ATCC Accession No. 37060) was inserted into the above-prepared cloning vector thereby to obtain expression vector YEp133PCT.

Figure 4:
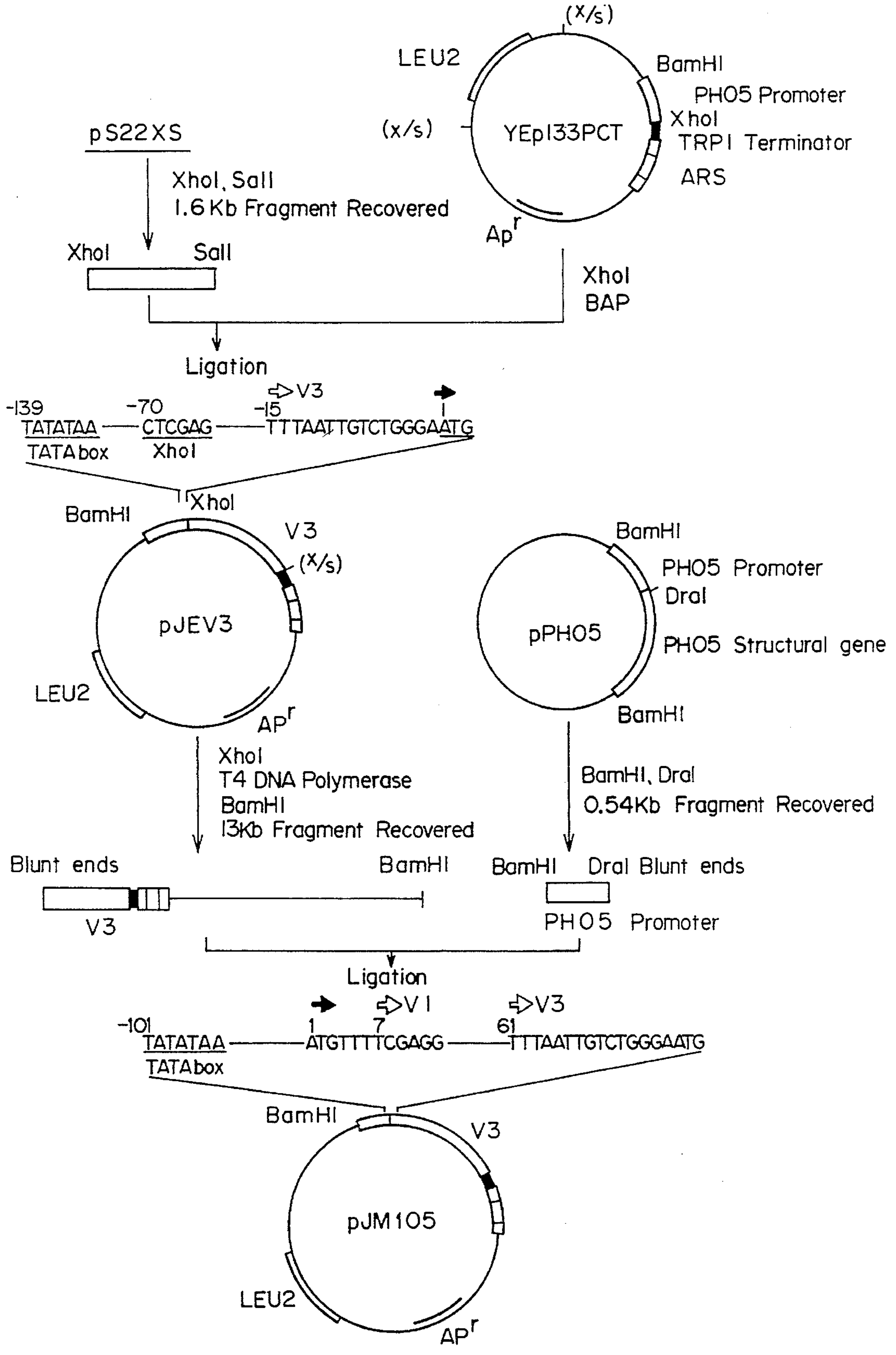
FIG. 4 shows a flow chart indicating the construction of pJM105.
Figure 5:
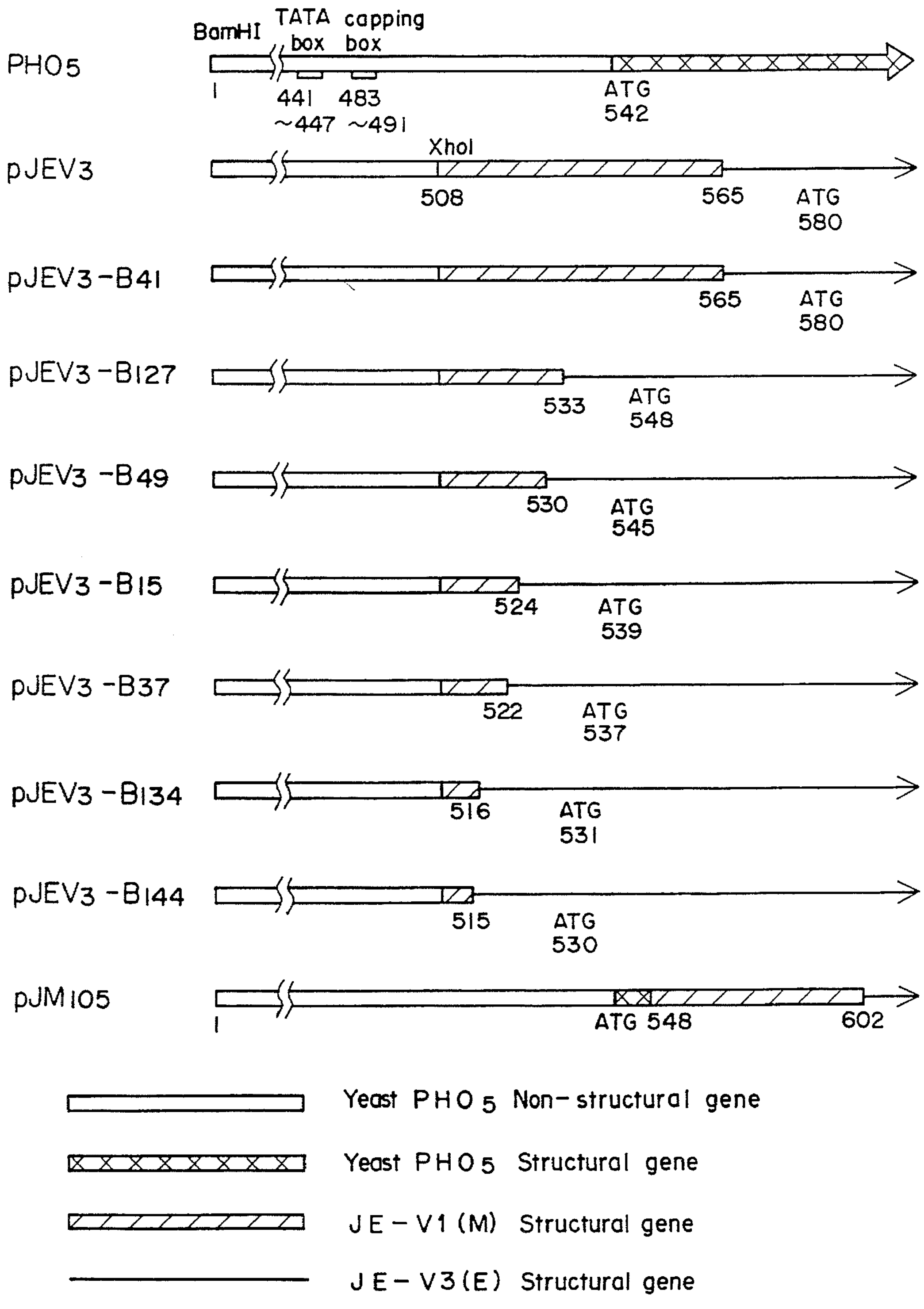
FIG. 5 shows structures of various reconstructed plasmids of pJEV3 and a structure of pJM105.

The cDNA of V3 protein gene was inserted into the thus obtained expression vector. Illustratively stated, pS22XS was digested with restriction enzymes XhoI and SalI, and the resulting mixture was subjected to agarose gel electrophoresis to recover a DNA fragment of about 1600 bp in molecular length. The recovered DNA fragment was ligated to the expression vector YEp133PCT at its XhoI site. *E. coli* strain JM83 was transformed with the resulting plasmid to form a transformant. The transformant was isolated and cultured in L-medium (1 w/v % bactotrypton, 0.5 w/v % yeast extract, 0.5 w/v % sodium chloride, 25 μg/ml ampicillin, pH 7.2–7.4). The plasmid was extracted from the transformant by the above-mentioned alkali extraction method. Then, the direction in which the DNA fragment containing the V3 gene was ligated to the YEp133PCT in the extracted plasmid was confirmed by digesting the plasmid with various restriction enzymes and subjecting the digestion mixture to agarose gel electrophoresis. The plasmid was designated plasmid pJEV3 (see FIG. 4). Yeast was transformed with the plasmid, and cultured. Production of the V3 protein in the incubated yeast was confirmed according to the ELISA method. Various trials were made in reconstructing the plasmid pJEV3 to increase the production efficiency of the V3 protein. The results are shown in FIG. 5. In particular, the pJEV3 DNA was digested with restriction enzyme XhoI, and both ends of the digested DNA were converted into blunt ends by the use of T4DNA polymerase. The resulting DNA was digested with restriction enzyme BamHI and subjected to agarose gel electrophoresis to recover a 13,000 bp-long DNA fragment. This DNA corresponds to the pJEV3 devoid of the PHO5 promoter region. On the other hand, to utilize the translation initiation codon ATG of the PHO5 structural gene, pPHO5 was digested with restriction enzymes BamHI and DraI, and the digestion mixture was subjected to agarose gel electrophoresis to recover a 550 bp-long DNA fragment of the PHO5 promoter region. The above-mentioned 13,000 bp DNA fragment was ligated to this 550 bp DNA fragment. *E. coli* strain JM83 was transformed with the ligated DNA, and cultured to clone the ligated DNA. The resulting cloned DNA was designated plasmid pJM105. The flow chart of FIG. 4 illustrates the procedures for preparing pJM105.

The use of the above-cloned pJM105 leads to the production of a polypeptide consisting of 519 amino acids and having such an amino acid sequence that the following amino acids are bonded in sequence in the order of:

(a) two amino acids, i.e., Met—Phe—, derived from PHO5;

(b) two amino acids, i.e., —Ser—Arg—, derived from the portion between the PHO5 promoter and the below-mentioned cDNA of V1 protein gene;

(c) 16 amino acids, i.e., —Arg—Val—Val—Phe—Thr—Ile—Leu—Leu—Leu—Leu—Val—Ala—Pro—Ala—Tyr—Ser—, derived from the cDNA of V1 protein gene lying upstream of the V3 protein gene in the genomic RNA of JE virus;

(d) 498 amino acids derived from the cDNA of V3 protein and having such an amino acid sequence that two amino acids, i.e., —His—Ala are deleted from the C-terminus of the amino acid sequence represented by the above-mentioned formula (I); and (e) one amino acid, i.e., —Ala derived from the universal terminator.

Step 6 [Transformation of yeast with the expression plasmid pJM105 and isolation of the transformed yeast]

The yeast *Saccharomyces cerevisiae* strain SHY4 (ATCC Accession No. 44772) was transformed with the expression plasmid pJM105 according to the alkali cation method. Illustratively stated, the yeast was cultured in YPD medium (2 w/v % bactopeptone, 1 w/v % yeast extract, 2 w/v % dextrose), and 5 ml of the culture was centrifuged at 2500 rpm for 5 min to harvest cells. The cells were suspended in 5 ml of TE buffer (10 mM Tris-HCl pH 8.0, 0.1 mM EDTA), and centrifuged to harvest cells. The cells were re-suspended in 0.6 ml of TE buffer. To 0.5 ml of the suspension was added 0.5 ml of 0.2M lithium acetate, and incubated at 30° C. for 60 min. Then, 8 μl of the plasmid DNA was added to 0.1 ml of the culture, and incubated at 30° C. for 30 min. To the resulting culture was added 0.1 ml of 70 w/v % polyethylene glycol 4000, and incubated at 30° C. for 60 min. Further, 2 ml of distilled water was added to the culture, followed by centrifugation at 2500 rpm for 5 min to harvest cells. The cells were re-suspended in a small amount of distilled water, inoculated to SD agar medium [0.67 w/v % bactoyeast nitrogen base amino acid free (manufactured and sold by Difco Co., U.S.A.), 2 w/v % dextrose, 20 μg/ml uracil, 20 μg/ml L-tryptophan, 20 μg/ml L-histidine, 2 w/v % agar] which is a selective medium not containing leucine, and incubated at 30° C. The colony formed by incubation was isolated to obtain a transformed yeast. The transformed yeast was designated SHY4/pJM105.

Step 7 [Incubation of the transformed yeast and extraction of the antigen]

The transformed yeast SHY4/pJM105 was inoculated to Burkholder medium, [which is a completely synthetic medium containing 1.5 g/l monobasic potassium phosphate (see Burkholder, P. R. et al., Am. J. Botany, 30, 206, 1943)], and incubated while shaking at 30° C. for 24 hr. After the incubation, the culture was centrifuged at 2500 rpm for 5 min to harvest cells. The cells were washed with distilled water once, inoculated to Burkholder medium containing 1.5 g/l potassium chloride in place of the above monobasic potassium phosphate, and incubated while shaking at 30° C. for 48 hr. After the incubation, the cells were harvested by centrifugation, washed and resuspended in 0.01M phosphate buffer (pH 9.0). Glass beads were put in the suspension, and vigorously shaken to disrupt the cells. The resulting suspension was centrifuged at 10,000 rpm for 10 min, and the supernatant was separated. Thus, there was obtained a yeast extract.

Step 8 [Antigen production efficiency of the transformed yeast]

The quantitative determination of the antigen in the yeast extract was carried out according to the ELISA method. ELISA titer was assayed by the sandwich method using as a catching antibody the purified IgG which was obtained from the serum of a mouse immunized with excess of Japanese encephalitis virus (Nakayama strain) and as a detecting antibody the HRPO (horseradish peroxidase)-conjugated anti-Japanese encephalitis V3 protein monoclonal antibody (see Kimura, K. J. et al, J. Virol. 45, 124, 1983). In effecting the assay of the ELISA titer, color reaction was developed by o-phenylenediamine, and the absorbance at 420 nm was measured. The ELISA antigen titer of a test specimen was determined using a reference Japanese encephalitis virus antigen R-181 (National Institute of Health of Japan) as a standard of 100 units. The results of the ELISA are shown in Table 1. From the assay, it was confirmed that the transformed yeast SHY4/pJM105 efficiently produced the antigen of the present invention.

TABLE 1

| Period of incubation (hr) | Cell population/ml ($\times 10^6$) | Antigen of the present invention (ELISA antigen titer) |
|---|---|---|
| 0 | 6.1 | 2.4 |
| 5 | 16 | 30 |
| 10 | 43 | 27 |
| 18 | 63 | 37 |
| 24 | 71 | 57 |
| 30 | 72 | 61 |
| 48 | 58 | 81 |
| R-181[1)] | | 100 |

[1)]Reference Japanese encephalitis antigen lot 181

Step 9 [Identification and molecular weight determination of the antigen produced by the transformed yeast SHY4/pJM105 according to Western blot ting technique]

Figure 6:
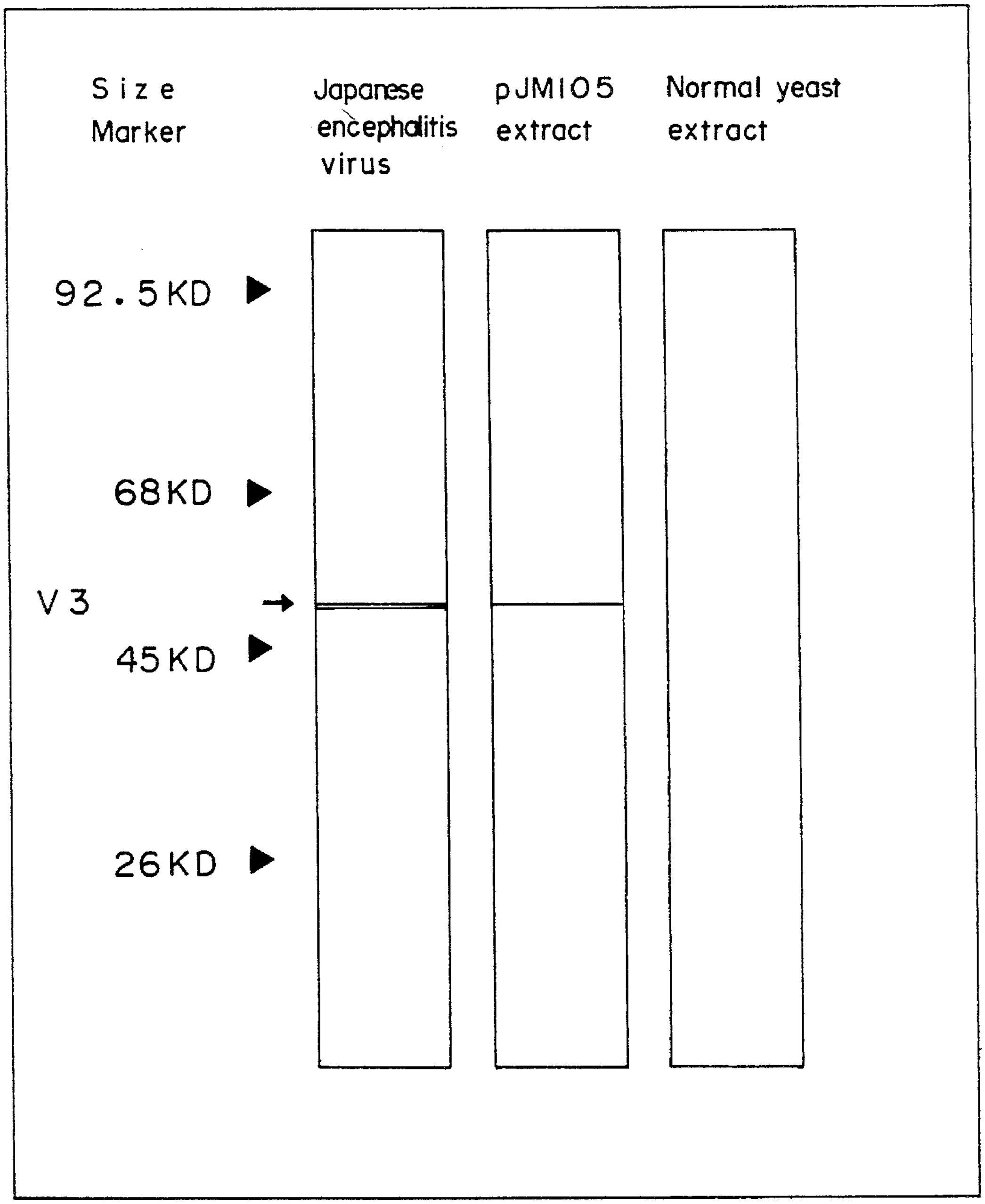
FIG. 6 is an illustration of the results of the electrophoresis for the identification of V3 protein of JE virus.

The antigen extract from the yeast was purified by centrifugation on 20–30 w/w % sucrose gradient at 21,000 rpm for 20 hr. The fraction containing a purified antigen of the present invention was put into 1 w/v % 2-mercaptoethanol/125 mM Tris-HCl (pH 6.8), kept at room temperature for 20 min, and subjected to electrophoresis on 10% polyacrylamide gel. The gel was taken off, and the protein on the gel was blotted onto a nitrocellulose membrane using the Trans-blot® cell manufactured and sold by Bio-RAD Co., U.S.A. The resulting nitrocellulose film was subjected to reaction with the above-mentioned anti-Japanese encephalitis virus V3 monoclonal antibody, and then to reaction with an HRPO-conjugated anti-mouse IgG goat IgG. Color reaction was developed by 4-chloroindonaphthol. Thus, identification of the antigen was made. FIG. 6 illustrates the reaction between a protein having a molecular weight of about 53 KD (kilodalton) and the anti-V3 monoclonal antibody. Since the molecular weight is in agreement with that calculated from the base sequence coding for a peptide containing the amino acid sequence as mentioned in Step 5, the protein was identified as an antigen containing such an amino acid sequence that the first and second amino acids counted from the C-terminus of the amino acid sequence of the V3 protein are deleted.

Step 10 [Immunogenicity of the present antigen produced by the transformed yeast]

The antigen extract obtained in Step 7 was centrifuged on 20–50 w/w % sucrose gradient at 21,000 rpm for 20 hr to obtain a partially purified antigen. The antigen was mixed with aluminum hydroxide as an adjuvant to obtain an antigen solution. The antigen solution was injected, in amounts of 4, 20 and 100 (ELISA antigen titer), intraperitoneally into each of 4 weeks-aged ddY mice to immunize them. A week later, the mice were immunized by injecting the antigen extract in the same amount. Further a week later, the blood was collected from each of the mice. With respect to the blood, the ELISA antibody titer against Japanese encephalitis virus was assayed according to the ELISA method as mentioned before and the neutralizing antibody titer against Japanese encephalitis virus was assayed according to the 50% plaque reduction method as mentioned before. The results are shown in Table 2. As shown in the table, the ELISA antibody titer of the antigen was detected by the ELISA method, but the neutralizing antibody titer was not detected in the above-mentioned immunizing method.

TABLE 2

| Adjuvant | Antigen titer[1)] | ELISA antibody titer | Neutralizing antibody titer[2)] |
|---|---|---|---|
| $Al(OH)_3$ | 100 | 100 | <1:10 |
| 0.2 mg/ | 20 | 51 | " |
| dose | 4 | 64 | " |
| (–) | 100 | 100 | <1:10 |
| | 20 | 54 | " |
| | 4 | 20 | " |
| R-181[3)] | 4 | 200 | |

[1)]ELISA antigen titer
[2)]according to the 50% plaque reduction method
[3)]Reference Japanese encephalitis antigen lot 181

Step 11 [Immunogenicity of the antigen produced by the transformed yeast]

The antigen solution prepared in substantially the same manner as in Step 10 was injected into the abdominal cavity of each of the mice 6 times at intervals of 7 days (1st, 8th, 15th, 22nd, 29th and 36th day). On the 43rd day, the blood was collected from each of the mice. The neutralizing antibody titer of the blood against JE virus was assayed using as the JE virus the Nakayama strain, Beijing strain and JaOArS982 strain, and the results are shown in Table 3. As shown in the table, with respect to all of the Nakayama, Beijing and JaOArS982 strains of JE virus, the neutralizing antibody was detected.

TABLE 3

| Adjuvant | Antigen titer[1)] | Neutralizing antibody titer[2)] Nakayama strain | Beijing strain | JaOArS982 strain |
|---|---|---|---|---|
| $Al(OH)_3$ | 100 | 1:117 | 1:48 | 1:59 |
| 0.2 mg | 20 | <1:10 | <1:10 | 1:11 |
| /dose | 4 | " | " | 1:10 |
| (−) | 100 | <1:10 | <1:10 | 1:15 |
| | 20 | " | " | <1:10 |
| | 4 | " | " | " |
| R-181[3)] | 4 | 1:3500 | 1:70 | 1:370 |

[1), 2), 3)]:As mentioned in Table 2

EXAMPLE 2

The *E. coli* strain JM83/pS22 obtained in Step 4 of Example 1 was cultured to obtain cells of the strain. From the thus obtained cells, the plasmid pS22 DNA was isolated by the alkali extraction method as described in Step 4 of Example 1. The isolated plasmid DNA was dissolved in an aqueous solution containing 10 mM Tris-HCl (pH 7.5), 100 mM NaCl and 7 mM $MgCl_2$. To the resulting mixture were added restriction enzymes MluI and SphI, followed by incubation at 37° C. for 2 hours, thereby to digest the plasmid DNA. The resulting mixture was subjected to agarose gel electrophoresis. From the resulting agarose gel, DNA fragments having a molecular length of about 1500 bp which contained a base sequence coding for JEV3 protein were recovered. The DNA fragments were digested using restriction enzymes in substantially the same manner as described above except that restriction enzymes NruI and DdeI were used instead of restriction enzymes MluI and SphI, thereby to obtain DNA digests. The thus obtained DNA digests were subjected to agarose gel electrophoresis. From the resulting agarose gel, DNA fragments having a molecular length of about 350 bp were recovered. The recovered DNA fragments were ligated to the vector YEp133PCT obtained in Step 3 of Example 1 at its XhoI site using an XhoI linker to obtain recombinants. The recombinants were transferred into cells of *E. coli* strain DH1 to obtain transformants. The selection of the transformant which contains the intended DNA fragment of about 350 bp from the above-obtained transformants was effected by colony hybridization method using as a probe $^{32}P$-labeled DNA coding for JEV3 protein. The $^{32}P$-labeled DNA was prepared as follows. First, the plasmid pS22XS obtained in Step 5 of Example 1 was digested with restriction enzymes XhoI and SalI, and the resulting mixture was subjected to agarose gel electrophoresis to recover a DNA fragment of about 1600 bp in molecular length. Second, the recovered DNA fragment was labeled with $^{32}P$ by means of nick translation using a nick translation kit N.5000 manufactured and sold by Amersham Japan Limited. Thus, there was obtained the above-mentioned $^{32}P$-labeled DNA.

The transformant selected by the above-mentioned colony hybridization method was cultured to obtain a clone of the transformant. From the clone, plasmids were isolated by the alkali extraction method as mentioned before. With the plasmids thus obtained, cells of the yeast strain SHY4 were transformed. The resulting cells were cultured on the SD agar medium as described in Step 6 of Example 1. The colony formed by culturing was isolated to obtain a transformed yeast.

The transformed yeast was used for the production of a polypeptide comprising a part of the amino acid sequence of the formula (I), which part consists of from 375th to 456th amino acids counted from the N-terminus of the amino acid sequence of the formula (I). In substantially the same manner as in Step 7 of Example 1, the transformed yeast was cultured to obtain yeast cells and from the thus obtained yeast cells, a yeast extract was obtained.

An aliquot of the yeast extract thus obtained was subjected to hemagglutination-inhibition (HAI) test according to the method of Clarke and Casals [American Journal of Tropical Medicine and Hygiene, 7, 561–573 (1958)] using 4 monoclonal antibodies respectively against 4 antigen determinant reagions (groups 1 to 4) of JEV3 protein [J. Kimura-Kuroda and K. Yasui, Journal of Virology, 45 (1), 124–132 (1983)]. The results are shown in Table 4 which will be given later. The results show that the yeast extract of the transformed yeast contains a substance which binds specifically with the monoclonal antibody against the antigen determinant region group 4 of JEV3 antigen. The plasmid contained in the transformed yeast was designated pV3G4-96 and the transformed yeast was designated yeast strain SHY4/pV3G4-96.

The yeast extract obtained above was subjected to purification in substantially the same manner as in Step 9 of Example 1 to obtain a purified antigen of the present invention.

EXAMPLE 3

Substantially the same procedures as in Example 2 were repeated to obtain DNA fragments having a molecular length of about 1500 bp which contained a base sequence coding for JEV3 protein. The DNA fragments were digested successively with restriction enzymes HpaII, Bal31 and StuI, thereby to obtain DNA digests. The DNA digests were subjected to agarose gel electrophoresis to recover DNA fragments of about 700 to 800 bp in molecular length. The recovered DNA fragments were ligated to the vector YEp133PCT at its XhoI site using an XhoI linker to obtain recombinants. The recombinants were transferred into cells of *E. coli* strain DH1 to obtain transformants. The selection of the transformant which contains the intended DNA fragments of about 700 to 800 from the above-obtained transformants was effected by colony hybridization method in substantially the same manner as in Step 1 of Example 2. Then, the thus selected transformant was cultured to obtain a clone of the transformant. From the clone, plasmids were isolated by the alkali extraction method as mentioned before. With the plasmids thus obtained, cells of the yeast strain SHY4 were transformed. The resulting cells were cultured on the SD agar medium as described in Step 6 of Example 1. The colony formed by culturing was isolated to obtain a transformed yeast.

The transformed yeast was used for the production of a polypeptide comprising a part of the amino acid sequence of the formula (I), which part consists of from 45th to 159th amino acids counted from the N-terminus of the amino acid sequence of the formula (I). In substantially the same manner as in Step 7 of Example 1, the transformed yeast was cultured to obtain yeast cells and from the thus obtained yeast cells, a yeast extract was obtained.

An aliquot of the yeast extract thus obtained was subjected to HAI test in the same manner as described in Example 2. The results are shown in Table 4 given below. The results show that the yeast extract of the transformed yeast contains a substance which binds specifically with the monoclonal antibody against the antigen determinant region group 1 of JEV3 antigen. The plasmid contained in the transformed yeast was designated pV3G1-38 and the transformed yeast was designated yeast strain SHY4/pV3G1-38.

The yeast extract obtained above was subjected to purification in substantially the same manner as in Step 9 of Example 1 to obtain a purified antigen of the present invention.

On the other hand, a yeast extract was obtained from cells of the yeast strain SHY4, retaining no plasmid, in substantially the same manner as in Step 7 of Example 1. The thus obtained yeast extract was used as control and subjected to HAI test in the same manner as described above. The results are also shown in Table 4.

TABLE 4

| | Yeast strain | HAI titer Monoclonal antibody group[1)] 1 | 2 | 3 | 4 |
|---|---|---|---|---|---|
| Example 2 | SHY4/pV3G4-96 | <10 | <10 | <10 | 10240 |
| Example 3 | SHY4/pV3G1-38 | 5120 | <10 | <10 | <10 |
| Control | SHY4 | <10 | <10 | <10 | <10 |

Note:
[1)]The group numbers of the monoconal antibody group correspond to those of groups of the antigen determinant regions reported in Journal of Virology, 45 (1) 124–132 (1983).

EXAMPLE 4

Step 1 (Construction of an expression plasmid for a V3 protein gene)

The clone S22XS prepared in Step 5 of Example 1 was digested with a restriction enzyme ScaI, thereby obtaining a DNA fragment of about 2.5 kb which comprises the 3-end region of the V3 gene containing a universal terminater (manufactured and sold by Pharmacia Fine Chemicals AB, Sweden) and a portion of vector pUC13.

On the other hand, the clone S22 prepared in Step 4 of Example 1 was digested with restriction enzyme ScaI, thereby obtaining a DNA fragment of about 2.4 kb which comprises the 3'-end region of the V2 gene, the whole of the V1 gene, the 5'-end region of the V3 gene and a portion of vector plasmid pUC13.

The above-obtained DNA fragments respectively of about 2.5 kb and about 2.4 kb were ligated to each other using a T4 ligase, thereby obtaining a plasmid pS22T.

Separately, plasmid pSV2neo [Mulligam, R. C. et al, Proc. Natl. Acad. Sci. U.S.A., 78, 2072 (1981)] was digested with NdeI. Then, both ends of the resultant plasmid DNA fragment were converted into blunt ends by the use of the T4 DNA polymerase. The resultant DNA was digested with BamHI, thereby obtaining a DNA fragment of about 2.6 kb containing the SV40 promoter, a gene for neomycin resistance and the poly A signal of the SV40.

On the other hand, plasmid pUC12 (manufactured and sold by Pharmasia Fine Chemicals AB, Sweden) was digested with BamHI and ScaI, thereby obtaining a DNA fragment of about 1.7 kb containing an origin of replication.

The above-obtained DNA fragments respectively of about 2.6 kb and about 1.7 kb were ligated to each other using T4 DNA polymerase, to thereby obtain a plasmid pUCsv-neo used for the gene expression in aminal cell.

The above-obtained plasmid pS22T was digested with HindIII, to obtain a DNA fragment of about 2 kb containing the V1 gene, V3 gene and universal terminater. The DNA fragment thus obtained was inserted in the HindIII site of the above-obtained plasmid pUCsv-neo. The resultant integrated plasmid was digested with PvuII, thereby obtaining a DNA fragment of about 2.4 kb. The thus obtained DNA fragment has an early promoter of SV40 upstream of the V1 and V3 genes. Thereafter, the DNA fragment was ligated to a DNA fragment obtained by BamHI-cleavage of plasmid pUCsv-neo, the both ends of which DNA fragment had been converted into blunt ends by means of T4 DNA polymerase, to thereby obtain an expression plasmid pJRME.

Figure 7:
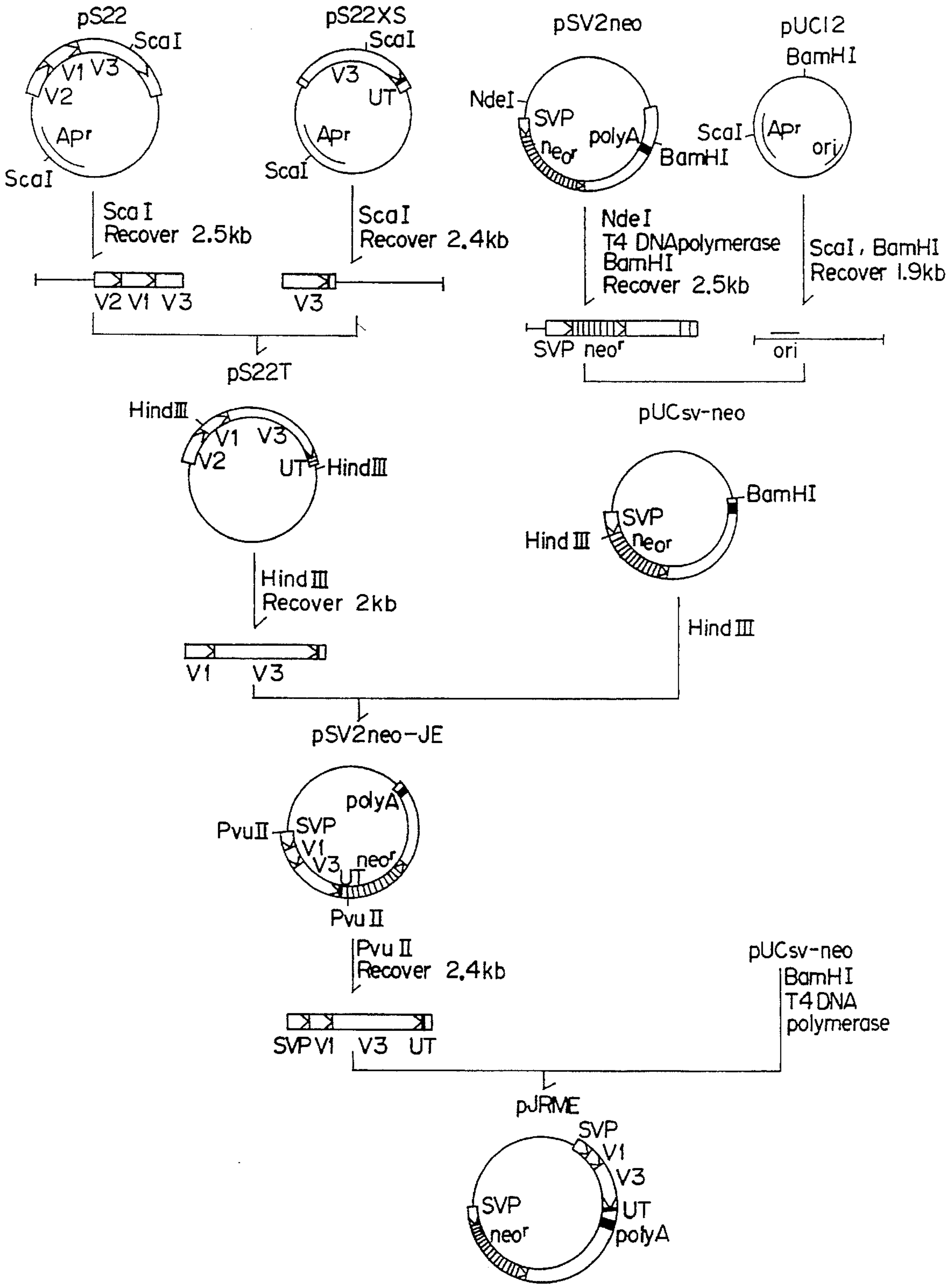
FIG. 7 shows a flow chart indicating the construction of plasmid pJRME.

The flow chart indicating the construction of the expression plasmid pJRME is shown in FIG. 7.

In FIG. 7, symbols V1, V2 and V3 respectively mean the V1 gene, V2 gene and V3 gene of Japanese encephalitis virus; $Ap^r$ and $neo^r$ mean an ampicillin resistance gene and a neomycin resistance gene, respectively; UT, SVP, poly A and ori mean a universal termination, an early promoter of SV40, a poly A signal and an origin of replication, respectively.

Step 2 (Transformation of a cultured animal cell with an expression plasmid pJRME and isolation of a transformed cell)

Cells of *Escherichia coli* strain JM83 were transformed with plasmid pJRME. The transformed cell was isolated and cultured in L-medium as described in Step 5 of Example 1. Then, from the cultured cell, a plasmid was extracted and purified in the same manner as in Step 5 of Example 1. Then, cells of an LLC-Mk2 cell line derived from monkey kidney were transformed with plasmid pJRME in accordance with the calcium phosphate method as follows. The LLC-Mk2 cell line was cultured in an MEM medium [Eagle, H., Science, 130, 432 (1959)] containing 5% FCS (Fetal calf serum). On the other hand, the plasmid pJRME DNA was dissolved in 2×HPS (50 mM HEPES (pH 7.1 ), 280 mM NaCl and 1.5 mM $Na_2HPO_4$). To the resultant solution an equi-volume of 250 mM $CaCl_2$ solution was dropwise added, and mixed. Then, the resultant mixture was kept at room temperature for about 30 min, thereby forming a complex of the DNA with calcium phosphate. The resultant DNA complex solution was dropwise added to a cell culture obtained by diluting three times and subcultured for about 6 hours, and the resultant cell culture was further incubated for about 16 hours. The culture medium of the resultant cell culture was replaced with an MEM containing 5% FCS and 800 μg/ml G418 (Geneticine, manufactured and sold by Sigma Chemical Company, U.S.A.), followed by incubation. After the incubation, the formed G418 resistant cells were cloned. Each of the thus obtained clones was cultured in the above-mentioned medium containing G418. The supernatant of each of the resultant cultures was subjected to measurement in accordance with the ELISA as described in Step 8 of Example 1. Based on the results of the assay, one clone producing the V3 protein was selected and designated "pJRME-H9/LLC-Mk2".

Step 3 (Cultivation of a transformed cell and extraction of the V3 protein)

The transformed cell clone pJRME-H9/LLC-Mk2 was cultured in a medium containing G418 as described in Step 2 of Example 4. The thus obtained cell suspension was subjected to centrifugation at 1500 rpm for 5 min, to collect a cell pellet. The collected cell pellet was suspended in 5 mM phosphate buffer containing 0.1% Tween 20. The resultant suspension was frozen at −70° C. and thawed at 37° C. The same freezing and thawing operation as mentioned above was further conducted twice. Then, the resultant suspension was subjected to centrifugation at 3000 rpm for 10 min. Thus, a supernatant was obtained as a cell extract containing the V3 protein.

The quantitative determination of the V3 protein in the above-obtained cell extract and the supernatant of the cell culture was conducted in accordance with the ELISA method as described in Step 8 of Example 1. The results are shown in Table 5.

TABLE 5

| Period of culturing (day) | Cell concentration (× $10^4$/ml) | ELISA antigen titer[4)] | |
|---|---|---|---|
| | | Cell extract | Supernatant of culture |
| 1 | 2.2 | 31.1 | 0.55 |
| 2 | 7.0 | 37.4 | 2.5 |
| 3 | 11.0 | 22.2 | 3.4 |
| 4 | 14.1 | 14.4 | 3.4 |
| 5 | 15.0 | 10.8 | 3.6 |
| 7 | 14.5 | 10.6 | 4.2 |

Note:
[4)]Relative to the antigen titer of Reference Japanese encephalitis virus antigen lot R-181, which titer is regarded as 100.

What is claimed is:

1. An isolated deoxyribonucleic acid which comprises a nucleotide sequence selected from the group consisting of a nucleotide sequence represented by the following formula (II) and the complementary nucleotide sequence to said nucleotide sequence of the formula (II):

TTT AAT TGT CTG GGA ATG GGC AAT CGT GAC
TTC ATA GAA GGA GCC AGT GGA GCC ACT TGG
GTG GAC TTG GTG CTA GAA GGA GAT AGC TGC
TTG ACA ATC ATG GCA AAC GAC AAA CCA ACA
TTG GAC GTC CGC ATG ATT AAC ATC GAA GCT
AGC CAA CTT GCT GAG GTC AGA AGT TAC TGC
TAT CAT GCT TCA GTC ACT GAC ATC TCG ACG
GTG GCT CGG TGC CCC ACG ACT GGA GAA GCT
CAC AAC GAG AAG CGA GCT GAT AGT AGC TAT
GTG TGC AAA CAA GGC TTC ACT GAT CGT GGG
TGG GGC AAC GGA TGT GGA CTT TTC GGG AAG
GGA AGC ATT GAC ACA TGT GCA AAA TTC TCC
TGC ACC AGC AAA GCG ATT GGA AGA ACA ATC
CAG CCA GAA AAC ATC AAA TAC GAA GTT GCC
ATT TTT GTG CAT GGA ACC ACC ACT TCG GAA
AAC CAT GGG AAT TAT TCA GCG CAA GTT GGG
GCG TCC CAG GCG GCA AAG TTT ACA ATA ACA
CCC AAT CGT CCT TCG ATA ACC CTC GGG CTT
GGT GAC TAC GGA GAA GTC ACG CTG GAC TGT
GAG CCA AGG AGT GGA CTG AAC ACT GAA GCG
TTT TAC GTC ATG ACC GTG GGG TCA AAG TCA

-continued

TTT CTG GTC CAT AGG GAA TGG TTT CAT GAC
CTC GCT CTC CCC TGG ACG TCC CCT TCG AGC
ACA GCG TGC AGA AAC AGA GAA CTC CTC ATG
GAA TTT GAA GAG GCG CAC GCC ACA AAA CAG
TCC GTT GTT GCT CTT GGG TCA CAG GAA GGA
GGC CTC CAT CAG GCG TTG GCA GGA GCC ATC
GTG GTG GAG TAC TCA AGC TCA GTG AAG TTA
ACA TCA GGC CAC CTG AAA TGT AGG ATG AAA
ATG GAC AAA CTG GCT CTG AAA GGC ACA ACC
TAT GGC ATG TGT ACA GAA AAA TTC TCG TTC
GCG AAA AAT CCG GCG GAC ACT GGC CAC GGA
ACA GTT GTC ATT GAA CTA TCC TAC TCT GGG
AGT GAT GGC CCC TGC AAA ATT CCG ATT GTC
TCC GTT GCG AGC CTC AAT GAC ATG ACC CCC
GTT GGG CGG CTG GTG ACA GTG AAC CCT TTC
GTC GCG ACT TCC AGT GCC AAC TCA AAG CTG
CTG GTC GAG ATG GAA CCC CCC TTC GGA GAC
TCC TAC ATC GTG GTT GGG AGG GGA GAC AAG
CAG ATC AAC CAC CAT TGG CAC AAA GCT GGA
AGC ACG CTA GGC AAG GCC TTT TCA ACA ACT
TTG AAG GGA GCT CAA AGA CTG GCA GCG TTG
GGC GAC ACA GCC TGG GAC TTT GGC TCC ATT
GGA GGG GTC TTC AAC TCC ATA GGA AAA GCC
GTT CAC CAA GTG TTT GGT GGT GCC TTC AGA
ACA CTC TTT GGG GGA ATG TCT TGG ATC ACA
CAA GGG CTA ATG GGT GCC CTA CTA CTC TGG
ATG GGC GTC AAC GCA CGA GAC CGA TCA ATT
GCT TTG GCC TTC TTA GCC ACA GGA GGT GTG
CTC GTG TTC TTA GCG ACC AAT GTG CAT GCT
..... (II)

wherein A represents a deoxyadenylic acid residue, G a deoxyguanylic acid residue, C a deoxycytidylic acid residue and T a deoxythymidylic acid residue, and the left and right ends of formula (II) represent the 5'-terminus and 3'-terminus, respectively, or a variant of said deoxyribonucleic acid which is obtained by modifying said .nucleotide sequences of the formula (II) in accordance with the degeneracy of the Genetic Code.

2. A recombinant DNA molecule which replicates in a host cell, which comprises a deoxyribonucleic acid according to claim 1 and a replicable expression vector.

3. A microorganism or cultured cell line transformed with a recombinant DNA molecule according to claim 2.

4. The microorganism *Escherichia coli* strain JM83/pS22 deposited at the Fermentation Research Institute under the accession No. FERM BP-1074.

5. The plasmid pS22.

* * * * *